US012746089B2

(12) United States Patent
Gill et al.

(10) Patent No.: US 12,746,089 B2
(45) Date of Patent: Sep. 29, 2026

(54) IMPLANTABLE GUIDE DEVICE

(71) Applicant: NEUROCHASE TECHNOLOGIES LIMITED, Bristol (GB)

(72) Inventors: Steven Streatfield Gill, Bristol (GB); Thomas Gill, Bristol (GB)

(73) Assignee: NEUROCHASE TECHNOLOGIES LIMITED, Bristol (GB)

( * ) Notice: Subject to any disclaimer, the term of this patent is extended or adjusted under 35 U.S.C. 154(b) by 6 days.

(21) Appl. No.: 18/288,775

(22) PCT Filed: Apr. 29, 2022

(86) PCT No.: PCT/GB2022/051104
§ 371 (c)(1),
(2) Date: Oct. 27, 2023

(87) PCT Pub. No.: WO2022/229662
PCT Pub. Date: Nov. 3, 2022

(65) Prior Publication Data

US 2024/0207010 A1 Jun. 27, 2024

(30) Foreign Application Priority Data

Apr. 30, 2021 (GB) ..................................... 2106203
Apr. 30, 2021 (GB) ..................................... 2106210
Apr. 30, 2021 (GB) ..................................... 2106224

(51) Int. Cl.
*A61B 90/11* (2016.01)
*A61B 90/00* (2016.01)
(Continued)

(52) U.S. Cl.
CPC ........... *A61B 90/11* (2016.02); *A61M 5/1413* (2013.01); *A61M 5/14244* (2013.01);
(Continued)

(58) Field of Classification Search
CPC ..................................................... A61B 90/11
See application file for complete search history.

(56) References Cited

U.S. PATENT DOCUMENTS 4,113,097 A 9/1978 Finn
4,629,451 A 12/1986 Winters et al.
(Continued)

FOREIGN PATENT DOCUMENTS

EP 2 653 130 A1 10/2013
EP 3119310 B1 5/2018
(Continued)

OTHER PUBLICATIONS

Extended European Search Report regarding Application No. 25193194.5, dated Oct. 6, 2025.
(Continued)

*Primary Examiner* — Christian A Sevilla
(74) *Attorney, Agent, or Firm* — Harness, Dickey & Pierce, P.L.C.

(57) ABSTRACT

A surgical guide hub for implanting in an aperture formed in a skull and made along a trajectory to a brain target, wherein the guide hub comprises: a through-bore for delivering a device therethrough and along the trajectory; at least one first formation on an external surface for securing the hub within the aperture in a skull; and at least one second formation on the surface of the through-bore for securing a guide device, an implantable device, or a cap to the hub. Also provided are a jig for setting the depth of insertion of a surgical tool into a patient during surgery, and a method of preparing an operative length of a surgical tool.

25 Claims, 24 Drawing Sheets

(51) Int. Cl.

| | |
|---|---|
| ***A61B 90/10*** | (2016.01) |
| ***A61M 5/14*** | (2006.01) |
| ***A61M 5/142*** | (2006.01) |
| ***A61M 5/145*** | (2006.01) |
| ***A61M 5/162*** | (2006.01) |
| ***A61M 5/168*** | (2006.01) |
| ***A61M 5/19*** | (2006.01) |
| ***A61M 5/38*** | (2006.01) |
| ***A61M 25/00*** | (2006.01) |
| ***A61M 39/02*** | (2006.01) |
| *A61M 25/06* | (2006.01) |

(52) U.S. Cl.

CPC ........ *A61M 5/14526* (2013.01); *A61M 5/162* (2013.01); *A61M 5/16881* (2013.01); *A61M 5/19* (2013.01); *A61M 5/385* (2013.01); *A61M 25/0015* (2013.01); *A61M 39/0247* (2013.01); *A61B 2090/062* (2016.02); *A61B 2090/0807* (2016.02); *A61B 2090/103* (2016.02); *A61M 2025/0046* (2013.01); *A61M 2025/006* (2013.01); *A61M 2025/0681* (2013.01); *A61M 2039/0205* (2013.01); *A61M 2039/025* (2013.01); *A61M 2039/0282* (2013.01); *A61M 2205/583* (2013.01); *A61M 2207/00* (2013.01)

(56) References Cited

U.S. PATENT DOCUMENTS

| | | | |
|---|---|---|---|
| 5,116,345 A | 5/1992 | Jewell et al. | |
| 5,865,842 A | 2/1999 | Knuth et al. | |
| 6,200,327 B1 * | 3/2001 | Assal | A61B 17/0469 606/148 |
| 6,942,667 B1 | 9/2005 | Song | |
| 9,393,216 B2 | 7/2016 | Woodrow et al. | |
| 12,478,370 B2 * | 11/2025 | DiGiovanni | A61B 17/0482 |
| 2001/0003156 A1 | 6/2001 | Gill | |
| 2003/0229354 A1 * | 12/2003 | Schmieding | A61B 17/866 606/99 |
| 2005/0251144 A1 | 11/2005 | Wilson et al. | |
| 2007/0265560 A1 | 11/2007 | Soltani et al. | |
| 2009/0248165 A1 | 10/2009 | Lin et al. | |
| 2013/0310767 A1 | 11/2013 | Solar et al. | |
| 2016/0263290 A1 | 9/2016 | Sarntinoranont et al. | |
| 2018/0206883 A1 | 7/2018 | McIntyre et al. | |
| 2019/0133708 A1 | 5/2019 | Manley | |
| 2019/0282262 A1 | 9/2019 | Bouazza-Marqouf et al. | |
| 2020/0337897 A1 | 10/2020 | Sacherman et al. | |

FOREIGN PATENT DOCUMENTS

| | | |
|---|---|---|
| JP | 2021-058620 A | 4/2021 |
| WO | WO-02/09622 A1 | 2/2002 |
| WO | WO-2013/050148 A1 | 4/2013 |
| WO | WO-2014/016591 A1 | 1/2014 |
| WO | 2019/088690 A1 | 5/2019 |

OTHER PUBLICATIONS

Huang et al., "Heterogeneously engineered porous media for directional and asymmetric liquid transport", Cell Reports Physical Science 3, 100710, Jan. 19, 2022.

Cherpinski et al., "High Performance Active Electrospun Polyhydroxyalkanoate Based Coatings", Conference: 15th TAPPI Advanced Coating Symposium Proceedings, Apr. 14-15, 2018, Charlotte, NC, USA.

Japanese Office Action regarding Application No. 2023-566953, dated Oct. 9, 2025, with English translation.

* cited by examiner

IMPLANTABLE GUIDE DEVICE

CROSS REFERENCE TO RELATED APPLICATIONS

This application is a U.S. National Phase Application under 35 U.S.C. 371 of International Application No. PCT/GB2022/051104, filed on Apr. 29, 2022, which claims priority to United Kingdom Application No. 2106203.9, United Kingdom Application No. 2106210.4, and United Kingdom Application No. 2106224.5, all filed on Apr. 30, 2021. The entire disclosures of the above applications are expressly incorporated by reference herein.

FIELD

The present invention relates to an implantable guide hub for use in neurosurgery, neurotherapeutics and neurodiagnostics. The invention also relates to a jig for setting the depth of insertion of a surgical tool into a patient during surgery. The device and jig are particularly useful in image-guided stereotactic neurosurgery where accurate and reproducible targeting is required.

BACKGROUND

In image-guided neurosurgical procedures targets within the brain and trajectories to them are identified on radiological images and their image based 3D coordinates are co-registered with the 3D coordinate system of a surgical targeting device or stereoguide. This registration is conventionally achieved with reference to fiducials, visible on radiological images that are attached to a base frame fixed to the patients head. The derived target and trajectory coordinates are set in the stereoguide which is then fixed to the base frame and instruments guided to the target. Alternatively so-called frameless registration can be achieved by mechanical means using an arm with position sensors or optically or electromagnetically tracked instruments to locate the position of radio-opaque markers that were fixed to the patient's head during image acquisition or to trace the patient's facial profile with their head fixed to an operating table. Stereoguides may include a moveable and lockable arc or an arm and may be a surgical robot. Targets in the brain can include anatomical structures or pathological structures such as tumours.

A number of difficulties can be encountered in image-guided stereotactic neurosurgery. These include targeting inaccuracy resulting in inadequate therapeutic gain and off-target side-effects. Inaccuracy can also result in higher rates of complication and morbidity through injury to vasculature with haemorrhage or injury to vital brain structures. Satisfactory fixation of stereotactically-inserted devices to the skull can be difficult and can present attendant risks of device pull-out or migration into the brain.

Current stereotactic systems are complex and require the surgeon to make multiple measurements and adjustments in order to deliver devices into the brain. The risk of human error is high and multiplied when more than one trajectory and target is required. The complexity of current stereotactic systems results in prolonged operation times which add additional risks such as higher rates of infection.

Current stereotactic systems do not fully satisfy the desire for accurate reproducibility in repeated procedures. Repeated procedures can be of particular benefit when optimising genetic therapies, delivery of chemotherapeutics and lesioning procedures, for example.

If an implanted device does become misplaced or is removed, re-insertion requires the whole surgical workflow to be repeated. This can include pre-operative imaging, planning the procedure, and application of a stereotactic system.

It is an object of the invention to address at least some of the aforementioned problems, by the provision of an improved apparatus and method for targeted neurosurgical procedures.

SUMMARY

According to a first aspect of the invention, there is provided a surgical guide hub for implanting in an aperture formed in a skull and made along a trajectory to a brain target, wherein the guide hub comprises:

- a through-bore for delivering a device therethrough and along the trajectory;
- at least one first formation on an external surface for securing the hub within the aperture in a skull; and
- at least one second formation on the surface of the through-bore for securing a guide device, implantable device, or a cap to the hub.

The guide hub may have a cylindrical or generally cylindrical body. The throughbore may be along the axis of the cylindrical or generally cylindrical body.

The through-bore may be aligned to deliver an implantable device along the trajectory, for example into the brain, by methods described herein. Thus, the throughbore of the guide hub can provide guidance for a device along the trajectory. Thus, the guide hub finds application in neurosurgery, but may also be employed in other surgical uses, where fixation of a guide hub to bone is desired.

The guide hub may be configured to provide guidance along a trajectory to a brain target. The guide hub typically provides a guidance element in the skull, as close as possible to a target in the brain, thereby assisting accuracy of guided delivery along a trajectory. The aperture formed in the skull penetrates the entire thickness of the skull. Therefore, the guide hub can typically be configured to provide access between the exterior of the skull and the interior of the skull. The through-bore of the guide hub is suitable for delivering a device through the skull and into the cranial cavity and/or the brain. In particular, fluid transfer tubes such as catheters and cannulas may be delivered through the guide hub into the cranial cavity and/or brain.

The guide hub does not comprise a guide tube such as in the prior art apparatus of FIG. 1 and described in US2001/0003156, but can be fitted with one as described hereafter. Thus, forces employed on insertion of the guide hub into an aperture in the skull are not transmitted by an attached guide tube to the brain.

The guide hub can be sized so that, when fitted to the skull of the patient, it does not protrude above the surface of the skull. Thus, guide hub can be for planting in an aperture formed in a skull at or below the skull surface. The guide hub can be of particular use when repeated procedures are envisaged. The guide hub may be closed with a cap fitting into the second formation and the scalp closed over it when not in use. When required to deliver a device, the scalp can be reopened, the cap removed, and the device delivered via the guide hub.

A wide range of devices can be delivered through the skull and into the cranial cavity and brain using the guide hub and systems described herein. Devices may include cannulas or catheters, for the delivery or removal of fluid for diagnosis or treatment; electrodes for recording, stimulating or blocking neural activity including radiofrequency lesioning; brachytherapy devices for delivering therapeutic radioisotopes; glass-fibres for delivering light, including laser, for lesioning or optic stimulation; probes for monitoring pressure, temperature, fluid flow, the concentration of metabolites or drugs or gasses; biopsy devices and stylets to provide markers in the brain or to maintain a track for later re-access of another device to a brain target.

More specifically, catheters and cannulas may be delivered through the guide hub into any intracranial space including into the ventricles, subdural or subarachnoid space, into abscesses, cysts, cavities and tumours as well as intraparenchymally. Fluids delivered for diagnostic purposes may include contrast agents visible on X-ray imaging including X ray computerised tomography (CT) and Magnetic Resonance Imaging (MRI), diagnostic radioisotopes and dyes. Fluids delivered for therapeutic purposes include, but are not limited to, chemotherapies, antibiotics, enzymes, neurotrophins, gene therapies, SiRNAs and antisense oligonucleotides, enzymes, immunomodulatory therapies (such as monoclonal antibodies and chimeric antigen receptor T-cell (CAR-T) therapy), Auger electron emitters, immunotoxins, molecular targeted therapies, monoclonal antibodies, oncolytic viruses, nanoparticles and botulinum toxin. Inert fluids (including artificial cerebrospinal fluid, normal saline, Hartmann's solution, Ringer's lactate) may also be infused for therapeutic purposes;

Devices may be delivered via the guide hub with the aid of a guide tube secured in the through bore.

Thus, the guide hub and associated systems and methods described herein can have application in a wide range of surgical methods and treatments. For example, surgical treatment of abnormalities of brain function, including, but not limited to, treatment of neurodegenerative and movement diseases such as Parkinson's disease, Alzheimer's Disease, Huntington's Disease, tremor, cerebral palsy; neuro-oncological diseases such as glioblastoma, cerebral metastases, diffuse pontine glioma; neuro-inflammatory diseases such as multiple sclerosis; psychiatric disorders such as depression and obsessive compulsive disorder; metabolic diseases such as lysosomal storage disorders; hydrocephalus and intracranial hypertension; and epilepsy.

The guide hub may be generally cylindrical in form. The hub may have an outside diameter of from 3 mm to 12 mm, advantageously, from 3 mm to 6 mm. The height of the hub may be from 3 mm to 10 mm, advantageously from 4 mm to 6 mm. Thus, the guide hub can provide a compact fitment into the skull of a patient.

The throughbore may be reduced in diameter at its distal end (distal to the outer surface of the skull in use). For example, it may have a diameter of from 0.5 mm to 5 mm or even from 1 mm to 3 mm. The reduced diameter can be chosen to provide a close fit to the device being delivered, or to an associated guide tube.

The guide hub may further comprise a seal located within the through-bore and configured to provide sealing engagement with a device passing therethrough or with a cap fitted to the through-bore and engaging with the second formation. The seal may be an O-ring seal or washer with a central aperture sized to receive a device, guide tube, or cap therethrough. The O-ring seal or washer may be configured to compress axially and expand radially to provide sealing engagement with a guide device, implantable device, or a cap to the hub in the central aperture.

The guide hub may have a conical distal end. The throughbore may have a conical distal end and may be configured to engage with a corresponding conical portion on a guide device, implantable device, or a cap to the hub to provide a sealing engagement therebetween.

The guide hub may include a proximal rim that may extend outwards of the hub to provide a lip for sitting on a surface about an aperture on a skull. For example, the proximal rim may extend from the hub by from 0.5 mm to 2 mm. Guide hubs where the proximal rim does not extend from the hub are also contemplated.

The guide hub includes a first formation on its external surface for the hub to engage with and become fixed within an aperture in a skull. The guide hub may be fitted to an aperture in a skull without the use of small screws or other separate fixings as are often employed when fitting surgical devices to bone. The guide hub may be press fitted into the skull aperture and so the first formation may take the form of one or more projections enabling the press fit action and/or preventing rotation of the guide hub once fitted.

Thus, the first formation on the external surface of the hub may comprise at least one broaching tooth for securing the hub to the skull. There may be a gap between the broaching tooth or teeth and a proximal rim to allow bone ingrowth into the gap when in use. The at least one broaching tooth or teeth may be of triangular cross-section and are configured to bite into and lock the hub into the surrounding bone in use.

Additionally, or alternatively, the first formation on the external surface of the hub may comprise at least one rib for securing the hub relative to the skull. The rib or ribs may extend generally axially along the surface of the guide hub, from proximal to distal end.

Other patterned surfaces may be employed to provide grip between the guide hub and bone. For example, a pattern of protuberances may be distributed about the outer surface of the guide hub.

Alternatively, the first formation on the external surface of the hub may comprise a screw thread for securing the guide hub to the skull.

The second formation, on the surface of the throughbore, is for securing a guide device, implantable device, or a cap to the hub. The second formation can allow releasable securing of a guide device, implantable device, or a cap to the hub.

Conveniently the second formation can also be used for securing a hub insertion tool to the hub. The hub insertion tool can comprise a rod with a formation at its distal end for engaging with the second formation in a hub. Thus the hub insertion tool constitutes a guide device that can be used with a stereoguide system to insert the hub into the skull along a trajectory as described further hereafter and with reference to particular examples.

Conveniently the hub insertion tool may be hollow along its length to allow insertion of a surgical tool or implantable device down through the hub insertion tool, through an attached hub located in a skull, and thence into the brain of a patient. In this way the combination of a guide hub and a hollow hub insertion tool (or another hollow elongate tool fitting to the second formation) can be used in combination as an elongate guide, fixed to the patient's skull, for insertion of tools or devices along a trajectory and into the patient. For example, a surgical tool such as a track making probe for making a track in the brain to enable and guide insertion of an implantable device can be delivered along the selected trajectory, via the hub and hub insertion tool combination, into a patient's brain as described further hereafter, with reference to a particular example.

An elongate guide, comprising a guide hub and a hollow hub insertion tool (or another hollow elongate tool fitting to the second formation); and methods for using the elongate guide; constitute further aspects of the invention. The hollow hub insertion tool (or another hollow elongate tool) may be provided with a hole at its distal end for venting air as a tool or device is delivered through it.

The second formation on a guide hub may comprise a screw thread configured to engage with a corresponding thread on an insertion tool, or to a guide device, implantable device, or a cap to be inserted in the throughbore. Alternatively, a bayonet type fixing between a device or cap and the second formation may be employed.

Where the second formation and guide device, implantable device, or a cap comprise screw threads, the corresponding screw threads may be formed to allow rapid fitting of the device or cap, for example with only a half turn rotation of the device or cap. Thus, the screw thread may be a double-entry thread comprising a first thread portion and a second thread portion, wherein each thread portion sweeps around half a revolution of the hub such that a device or cap can be inserted fully within the thread and locked securely therein by a half turn rotation.

The corresponding screw threads may be locking screw threads. For example, locking screw thread arrangements such as those of the Spiralock® type that make use of relatively free running threads that lock when a male thread engages a wedge ramp at the root of the female thread. For further example, at least one of the first thread portion and second thread portion may comprise a notch configured to temporarily lock a device or cap within the first or second thread portion by engagement of the notch with a corresponding rib on the device or cap. Each of the first and second thread portions may comprise a notch configured to temporarily lock a device, cap within the first and second thread portions by engagement of the notches with corresponding ribs on the device or cap.

Thus, the second formation can be used for rapid (e.g., half turn) screw fixing of a guide device, implantable device, or a cap to the guide hub, which can be done with a simple screwdriver tool with an end shaped for locating into a suitable formation on the device or cap. Conveniently the engagement between the screwdriver end and the formation on the guide device, implantable device, or a cap provides a releasable attachment. For example, the end of the screwdriver may be an interference fit with the formation on the device or cap so that the device or cap remains attached to the screwdriver until fitting to the guide hub is complete. Where the device being fitted is elongate and is to extend beyond the guide hub after fitting (e.g., a cannula for delivering a therapy as an infusate), the screwdriver tool may be hollow along its length to allow passage of the device therethrough. Where the screwdriver is hollow along its length, a vent hole may be provided at or near the distal end for venting air as a device or surgical tool is passed through the body of the tool and into a patient. This can aid in prevention of driving air into a patient, e.g., into a patient's brain. Alternatively, a screwdriver tool can be provided with distal (head) end that can accept an elongate device into a side slot and then passing through the extreme distal end of the tool, as described in more detail hereafter. The side slot can also act as an air vent. The side slot may extend to the extreme distal end of the screwdriver tool. This can allow easier fitting and removal of elongate devices such as cannulas as described further hereafter. The screwdriver tool constitutes another aspect of the invention.

The guide hub of the invention is for delivering a device through the throughbore and along a trajectory. The second formation on the surface of the through-bore is for securing a device or cap to the hub. A cap secured to the second formation may secure a device to the hub. Thus, the present invention also provides a system comprising a surgical guide hub according to the invention as described herein; and a device or cap configured to engage and preferably to also lock within the through-bore of the hub.

The device or cap may comprise a seal to provide sealing engagement with the through-bore of the hub. Alternatively, or additionally the seal may be provided on the throughbore.

The device or cap of the system may comprise a conical portion which is configured to engage with a corresponding conical portion of the hub to provide a seal therebetween.

The device or cap may comprise a screw thread configured to engage with a corresponding screw thread of the second formation on the through-bore of the hub.

Thus, the device may comprise a formation for securing into the second formation in the guide hub (e.g., a formation comprising an external thread may be secured about the body of the device).

A cap of the system may be for sealing the throughbore when entry to the cranial cavity is not required.

Alternatively, the cap may have a cap throughbore passing therethrough, which may be for securing an implantable device to the guide hub. For example, a cannula may pass freely though the cap throughbore. As the cap is secured e.g. screwed into the throughbore, the cannula can be gripped by an O ring seal within the throughbore that is compressed axially and expanded radially inwards by the cap.

The guide hub of the invention is implanted into an aperture of the skull in use. The guide hub acts as a guide for insertion of devices into the cranial cavity and in particular along a trajectory to a target in the brain. Following imaging and use of a stereotactic system to determine the trajectory, the general procedure employed to insert the hub may include the steps of:

- exposing the skull by an incision in the scalp;
- machining a flat face on the skull with a facing tool;
- drilling a pilot hole through the skull along the trajectory;
- enlarging the pilot hole to provide a profiled aperture to accept a guide hub; and
- press or screw fitting the guide hub into the profiled aperture.

The flat face made by the facing tool provides a surface, generally perpendicular to the trajectory, that allows drilling of the pilot hole whilst avoiding slippage of the pilot hole drill, which could occur if applying the pilot drill directly to the curvature of the skull surface.

Thereafter the guide hub is employed for insertion of a device. The preparation of the profiled hole, fitting of the guide hub, and delivery of a device, especially into the brain, requires careful guidance and accuracy throughout the procedure, including making use of stereotactic means such as stereotactic frames or robot arms.

Using conventional methods of drilling on the surface of the skull to form a profiled hole and fit devices into the brain typically requires many measurements to be taken, particularly when multiple different pieces of equipment are used to form the hole for the introduction of a hub or other apparatus.

When using conventional stereoguides, brain images are registered with the stereotactic reference system and the stereoguide is set to the target coordinates and along the desired trajectory. The stereoguide has its own datum point from which the target is at a measured distance along a selected trajectory. Currently available stereoguides have for example distances of 190 mm or 160 mm between the datum and the target. Robotic stereoguides can be pre-set with a desired distance between the datum of the robotic stereoguide and the target.

Brain imaging provides the skull thickness along the desired trajectory and the distance from the skull surface to the target. In conventional methods, this information is used to allow the surgeon to calculate the length of each piece of apparatus to be introduced along the trajectory into the head of the patient. For example, the surgeon will calculate that a particular depth into the brain must be reached by a first device and will therefore cut or adjust the length of the first piece of apparatus to allow that depth to be reached when using the stereoguide method. The next device to be introduced may be required to reach a different depth, often deeper into the brain. The surgeon will again use the data from the imaging to calculate the length the second device must be adjusted or cut to and make the adaption so that the desired depth is reached when using the stereoguide. This process can be laborious and requiring many calculations with the attendant risk of human error, particularly in the stressful and fatigue inducing environment of neurosurgery.

According to a further aspect the present invention provides a jig for setting the depth of insertion of a surgical tool into a patient during surgery, the jig comprising:

a tool aligning device;

a representative datum representing a stereoguide datum; and a reference guide moveable relative to the representative datum to set a baseline length from the representative datum to a datum surface on the reference guide;

wherein the reference guide comprises at least one offset from the datum surface configured to receive a surgical tool extending from the tool aligning device; and wherein the depth of insertion of the surgical tool when used in surgery on a patient is set on the jig by the distance from the representative datum to the offset.

The jig may also be used for setting the depth of insertion of a device into the patient, such as any of the devices (cannulas, catheters, DBS electrodes etc) discussed herein with respect to use of the guide hub of the invention. Thus, the jig can be used in the insertion procedure and uses of the guide hub of the invention as described herein, but can also find more general use in neurosurgery and other surgical procedures. The datum surface on the reference guide represents the skull of a patient or any other surface or datum used in a surgical procedure, for example a datum based on the location of a guide hub of the invention in a patient's skull.

The jig and associated tools described herein have the advantages that only a limited number of measurements or calculations of length are required. For example, only one baseline measurement may be required to prepare a jig for setting all the tools and device lengths or depths required for a complete surgical procedure. Furthermore, the tools and devices required for a procedure can be set in the jig ready to be transferred to the patient one after another, with minimal handing, thereby reducing the risk of the transfer of infection.

The jig may also comprise a target datum, representing a target position with respect to the stereoguide datum as used in a chosen stereotactic system or arrangement. Thus, the distance from the representative datum to the target datum on the jig corresponds to the stereoguide datum to target distance when carrying out a surgical procedure on a patient. For the commercially available Cosman Roberts Wells (CRW) stereotactic frame that distance is set at 160 mm from the target and the corresponding distance for a Leksell frame is 190 mm. The datum surface on the reference guide can therefore represent the skull surface, interposed between the representative datum and the target datum on the jig.

The jig may be generally rectangular in form. The jig may take the form of an open frame onto which surgical tools are placed. The jig may be provided with a back plate. The jig may be provided with a stand to hold the jig up from an angle to the horizontal (for example at 45 degrees).

The tool aligning device may comprise the representative datum.

The tool aligning device may comprise grooves provided on a back plate. The tool aligning device may comprise a bar including slots or grooves to receive generally elongate tools and direct their distal ends towards the reference guide. The reference guide may be in the form of a bar parallel to the bar of a tool aligning device. The reference guide may be moveable relative to the tool aligning device whilst retaining the parallel relationship.

In the jig, the reference guide is moveable relative to the representative datum. Conveniently this is achieved by having the reference guide moveable, and the representative datum fixed. For example, a representative datum may be provided as part of a tool aligning device in a fixed position in the jig. However, alternative arrangements are contemplated, for example where the reference guide and its associated datum surface are fixed; and the representative datum is moveable to set the baseline length. For example, the representative datum may be provided on a moveable tool aligning device. As a yet further example both the representative datum and the reference guide may move when setting the baseline length.

In a convenient form of the jig, the tool aligning device comprises a bar including slots or grooves to receive generally elongate surgical tools and direct their distal ends towards the reference guide;

the reference datum is provided on the bar of the tool aligning device;

the reference guide comprises a bar parallel to the bar of the tool aligning device and is moveable relative to the tool aligning device whilst retaining the parallel relationship; and the bars of the tool aligning device and the reference guide are connected by at least two rails, the at least two rails disposed one at each end of the bar of the tool aligning device and connecting to corresponding ends of the bar of the reference guide.

In this form it can be particularly convenient for the tool aligning device (and associated reference datum) to be fixed and the reference guide moveable.

The jig may also comprise one or more cross members to provide bracing, for example extending between the at least two rails at each of their ends.

The bar of the reference guide may be in sliding engagement with the at least two rails and may be clampable to one or more of the rails to set the baseline length. There may be at least three rails connecting the tool aligning device and the reference guide, with the third rail disposed at a midpoint of the bar of the tool aligning device and at least extending to a corresponding midpoint of the bar of the reference guide.

As an alternative to sliding engagement between the rails and a moveable reference guide, the at least two rails may be threaded and operate as leadscrews passing through corresponding threads on the bar of the moveable reference guide; or the at least two rails may comprise rack gears and the bar of the moveable reference guide comprises corresponding pinions.

The jig may be motor driven; and may be computer controlled to set the baseline distance. The setting of the jig may even be directly from the surgical planning software. From the planning scan, information such as the target location relative to skull, the thickness and the skull and a trajectory from the skull to a target are obtained. Therefore, a jig may be set by computer control using scan data as input, prior to the surgical procedure. For example, by servomotors driving spindle shafts controlled by the computer.

In the jigs of the invention, the reference guide may comprise at least one guide channel extending therethrough, for passage of a surgical tool or device, the guide channel extending from the datum surface and continuing in the direction set by the tool aligning device. This allows the length of a device from the datum surface to be measured and adjusted or cut to a length as required, for example the required length of a cannula that in use will extend below a guide hub into the brain of a patient.

The jig allows setting of tools for creating a profiled hole in a skull and also the lengths of devices to be inserted into a skull, all determined from one setting of the baseline length and the scan data used when determining the trajectory and distances to target when planning surgery.

For use in the insertion of a guide hub in accordance with the present invention, or in similar surgical procedures where a hole is prepared in bone, the tool aligning device may be configured to receive one or more of:

a facing tool for creating a flat worksurface on a bone;

a pilot drill for creating a pilot hole in a bone;

and a core drill for creating a profiled hole in a bone.

The reference guide may further comprise a hole for receiving a surgical guide hub of the invention. This can be used to set tools and devices on the jig before transferring them to a patient. Thus, the reference guide may include a guide channel therethrough for passage of a surgical tool through the moveable reference guide and a surgical hub located in the hole.

The jig may further comprise a moveable cutting or depth measuring guide disposed further from the tool aligning device than the reference guide and configured for adjusting a tool or device to a selected length or for cutting a tool or device to a selected length (extending from the datum surface through the moveable reference guide). The moveable cutting or depth measuring guide may comprise a bar parallel to both the aligning device and the reference guide and have a guide surface for engaging with the distal end of a device or device part. The guide surface can be set at an appropriate distance from the datum surface on the reference guide to measure or cut to length a device that passes into the skull from a guide hub. The moveable cutting or depth measuring guide may comprise a slot, transverse to the direction of a device placed in the jig, to allow insertion of a knife for cutting the device to a selected length.

According to another aspect the present invention provides a system comprising a jig of the invention and further comprising:

at least one surgical tool selected from the group consisting of:

a facing tool for creating a flat worksurface on a bone;

a pilot drill for creating a pilot hole in a bone;

a core drill for creating a profiled hole in a bone;

a guide hub as described herein for insertion into the profiled hole.

According to another aspect the present invention provides a method of preparing an operative length of a surgical tool, comprising the steps of:

i) providing a system comprising the jig of the invention and at least one surgical tool;

ii) setting a baseline length from the representative datum to a datum surface on the reference guide by moving the reference guide relative to the representative datum;

iii) moving the surgical tool in the tool alignment device into a pre-determined offset in the reference guide to obtain an operative length of the surgical tool.

The step of setting the baseline length may comprise:

iv) holding a datum measurement tool within the tool alignment device;

v) moving the reference guide relative to the tool alignment device to contact the distal end of the datum measurement tool; and vi) clamping the reference guide stationary at the length from the representative datum determined by the datum measurement tool.

The jig and associated methods can find use in implantation of other devices into the skull of a patient. For example, in Deep brain Stimulation (DBS) procedures. In particular for fitting a skull mounted Deep Brain Stimulation (DBS) battery power supply (a 'generator').

DBS generators are used to power DBS electrodes fitted into the brain of a patient. Conventionally, DBS generators are mounted in the chest wall of patients, with wiring running subcutaneously to supply power to DBS electrodes at the skull via the neck. DBS generators may comprise a removable battery or may be rechargeable and for example charged wirelessly by inductive charging.

Where DBS generators are mounted close to the DBS electrodes, such as in the skull of the patient, they are typically rectangular or square in form. To install such DBS generators, the surgeon must make a correspondingly shaped hole in the skull of the patient, which is time consuming. A jig of the present invention can be used to aid in preparing a hole in the skull of the patient and fitting of a cylindrical DBS generator as described in more detail hereafter and with reference to particular embodiments.

According to another aspect the present invention provides a system for implantation of a cylindrical DBS generator in the skull, the system comprising:

a) a jig of the invention as described herein;

b) a facing tool for creating a flat worksurface on a bone;

c) a pilot drill for creating a pilot hole in a bone;

d) a core drill for creating a hole larger than the pilot hole in a bone; and e) at least one milling tool for creating a profiled hole of a larger diameter than the core drill hole to accommodate a said cylindrical DBS generator within the skull.

The milling tool may include a distal cutting surface for cutting a DBS generator mounting hole of a larger diameter than the core drill hole through the skull and a proximal cutting surface for creating a ledge in the skull around the DBS generator mounting hole to accommodate a corresponding lip of the cylindrical DBS generator. Alternatively, two milling tools may be employed, having different diameters, to cut a profiled hole including a ledge to accommodate a corresponding lip of the cylindrical DBS generator.

The system may further include a blunt hook used to free dura from under the inner table of the skull, following completion of the core drill hole. A haemostatic gel such as a DuraSeal® gel may also be provided and is injected into the extradural space to provide a protective barrier preventing tearing of the dura when the milling tool is used.

The present invention also provides methods of surgery making use of one or more of the guide hubs, the jigs, and the associated tools and devices as described herein.

BRIEF DESCRIPTION OF THE DRAWINGS

Embodiments of the invention will now be described with reference to the following drawings, in which.

DETAILED DESCRIPTION OF THE DRAWINGS

Figure 1A:
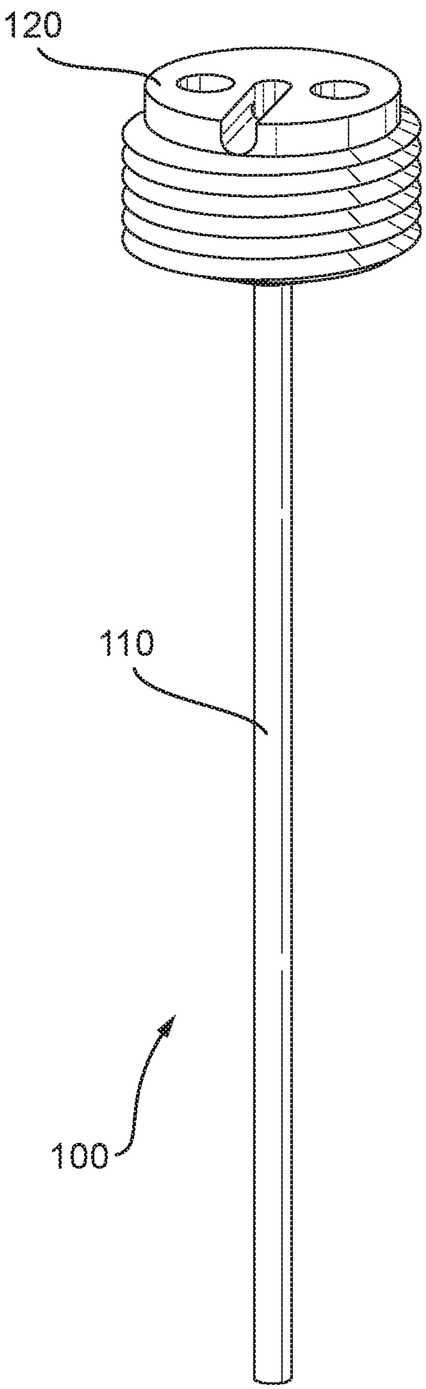
FIGS. 1*a* and 1*b* show a prior art guide device.
Figure 1B:
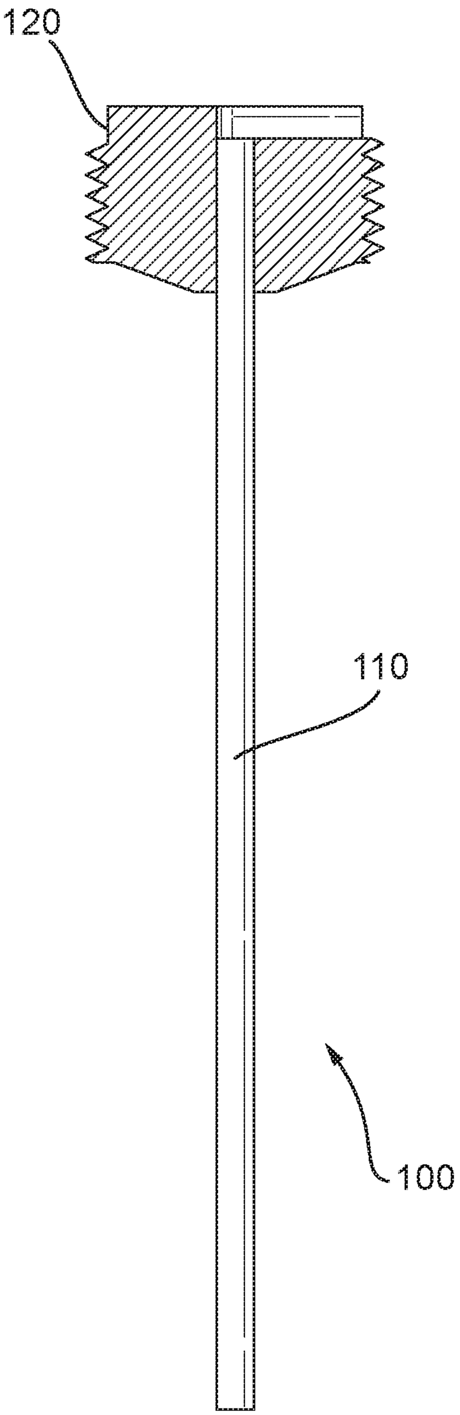

FIGS. 1*a* and 1*b* show a prior art guide device 100 in isometric and cross-sectional views respectively, comprising a tube 110 that has a hub 120 attached to a proximal end thereof. The hub 120 has a passageway therethrough in communication with the bore of the tube 110 and has a screw thread on its external surface.

The guide device 100 is installed for use in the skull of a patient by first drilling a hole along a desired trajectory in the skull guided by a stereoguide. The guide device's tube 110 is cut to an appropriate length to provide access to a brain target e.g., for a cannula to be delivered through the tube 110. The tube 110 is delivered over a probe that is guided by the stereoguide through the hole formed in the skull such that when the distal end of the tube is at its planned location the guide device's hub 120 is secured in the pre-formed hole in the skull. With an appropriately sized drill hole the fixation may be a press fit or if pre-tapped it may be a screw fit or alternatively it may be bonded in the drill hole with acrylic cement. The probe is removed and the guide device 100 can remain, installed, at least temporarily, in the head of a patient to allow other neurosurgical apparatus such as a cannula to be guided therethrough to reach targets within the brain.

In some circumstances, the guide device 100 may be left in the skull and brain of a patient for a prolonged period of time. The guide device 100, which is fixed to the skull, does not move with the brain as the brain moves within the skull. Therefore relative movement of the brain against the tube 110 of the guide device 100 may occur and cause trauma to the brain tissue in the locality of the tube 110. The guide device 100 does not provide a seal between its bore and the surgical device that passes there through. There is thus a space between the guide device 100 and a surgical device through which infection can potentially enter into the brain. The guide device 100 does not provide a means of securing a surgical device that is delivered through its bore. For example, when the guide device 100 is used to deliver a Deep Brain Stimulation (DBS) lead, the lead is bent through 90° as it exits the hub 120 of the guide device 100 and is fixed to the skull by compression under a bone plate secured to the skull with small screws. This fixing process is awkward to carry out and carries the risk of inadvertently moving the DBS lead from its target location.

Figure 2A:
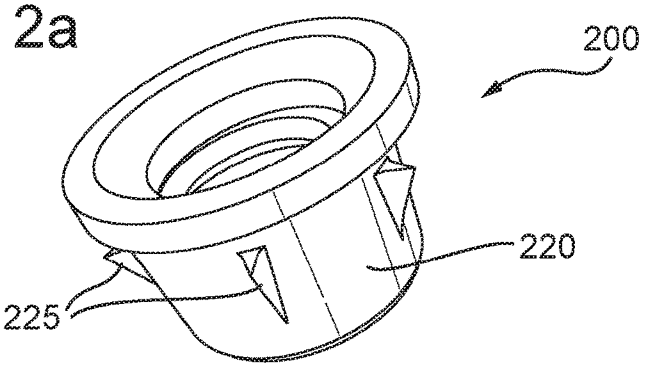
FIGS. 2*a*-2*f* show features of a guide device in accordance with the present invention.
Figure 2B:
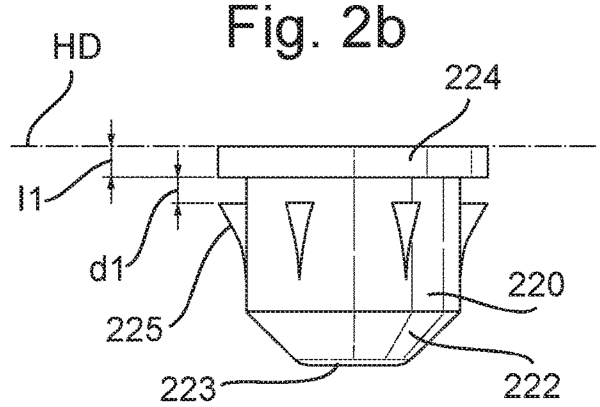
Figure 2C:
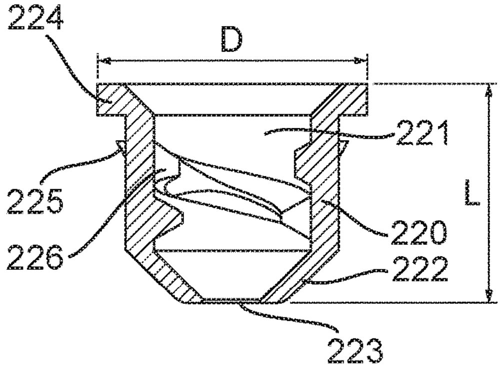

FIGS. 2*a* and 2*b* show a guide device 200, in accordance with the present invention. FIG. 2*c* shows a similar guide device 200 to that of FIGS. 2*a* and 2*b* in cross sectional view. The example of FIG. 2*c* differs by having smaller broaching teeth 225 as discussed further below. The guide devices 200 are configured to be implanted within the skull of a patient to provide a low profile access point for introducing apparatus into the brain, along a selected trajectory. the device 200 also provides means for securing the apparatus to the guide device 200.

The guide devices 200 comprise a guide hub 220 but do not comprise a guide tube 110 as in the device of FIGS. 1*a* and 1*b*.

The guide hubs 220 may be made of titanium or PEEK (polyether ether ketone) or another biocompatible material. A PEEK hub has the advantage of being a long-term implantable device that causes no artefact when imaged with MRI and will not heat up in a high magnetic field. Each hub 220 comprises a through-bore 221 and has a conical portion 222 at its distal end with a central hole 223 that forms the extreme end of the through-bore 221. The hubs 220 further comprise a proximal rim 224 at its proximal end. As will be explained in more detail later, the rim 224 provides a hub datum HD, allowing the distance between the hub datum HD and a brain target to be calculated.

The main bodies of the hubs 220 have a diameter (D) and length (L). The diameter of the hub 220 through bore 221 and distal central hole 223 can be sized for guiding and securing a range of surgical devices, for example ranging in diameter from 0.5 mm to 5 mm. By way of example the dimensions of a guide hub 200 for use in delivering and securing a device with a cross section diameter of 1.2 mm may have a diameter (D) of the main body of the hub 220 of around 4 to 5 mm. The hub 220 may be of a length (L) such that it can be fully implanted within the thickness of the skull of the majority of adults and children. Thus the length (L) may be around 4 to 5 mm. The through-bore 221 may be around 3 mm in diameter at the proximal end of the hub 220. The central hole 223 at the extreme end of the through-bore 221 may be typically about 1.2 mm in diameter. The rim 224 may be around 0.5 mm in length (l1) and 0.5 mm thick, with an outside diameter of around 5 mm and an inside diameter of around 4 mm. Guide hubs 220 with alternative dimensions are envisaged for use in delivering devices with different diameters to the brain in humans and other animals, or when employing them in other parts of the human body.

As can be seen in FIGS. 2*b* and 2*c*, in these examples, the conical portion 222 tapers at an angle of around 45° over a length (L) of around 1 mm. This provides an angled surface of about 45° on the outside for the hub 220 and a similarly angled inner surface, which provides a surface for apparatus to sit within the hub 220.

Referring to FIGS. 2*a*, 2*b* and 2*c*, the hubs 220 comprise broaching teeth 225 for preventing rotation of the hub 220 when fixed to the skull. The broaching teeth 225 may start a distance (d1) from the rim 224 to allow bone to regrow within this gap when installed in the skull and thereby provide a stable long-term implant. The distance (d1) may provide a gap between the rim 224 and the broaching teeth 225 of 0.5 mm, for example. In some embodiments, the broaching teeth 225 may extend to a similar width as that of the outside diameter of the rim 224, as can be seen in FIG. 2*b*. In FIG. 2*c* smaller broaching teeth are illustrated.

In the examples shown in FIGS. 2*a*, 2*b* and 2*c*, the hub 220 is provided with six broaching teeth 225 which are equally spaced around the hub 220. The shape and angle of the broaching teeth 225 may be adjusted from that shown in the examples in the figures to allow insertion into different bone densities or bones of different strengths. In the examples broaching teeth 225, each have a triangular cross-section which is configured to bite into and lock the hub 220 into the surrounding bone as the hub 220 is driven into the bone. Other means for prevention of rotation of the hub in a skull can be provided, for example ribs such as axially extending ribs, disposed around the circumference of the hub.

As an alternative to broaching teeth 225, a guide hub 220 may be provided with an external thread which is arranged to bite into the skull or the hub may have an interference pattern (not shown). The interference pattern, such as an array of protrusions, can provide for an interference fit to provide locking of the hub 220 into the surrounding bone as the hub 220 is pushed into the bone.

Figure 17A:
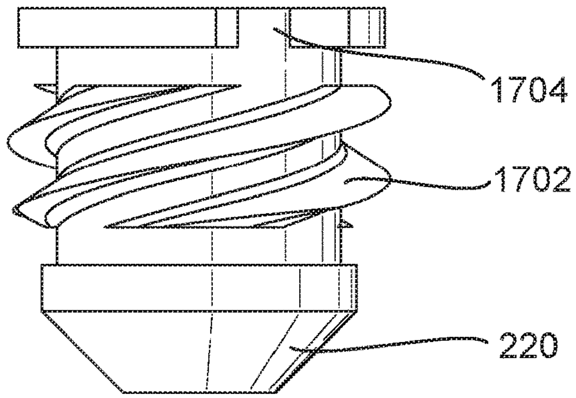
FIGS. 17*a* to 17*c* show a guide device having an external self-tapping thread and hub engagement features.
Figure 17B:
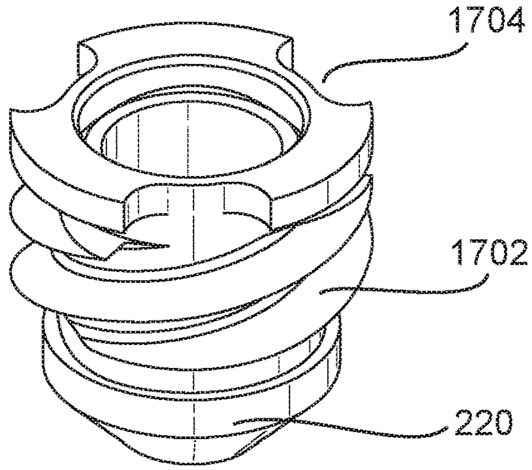
Figure 17C:
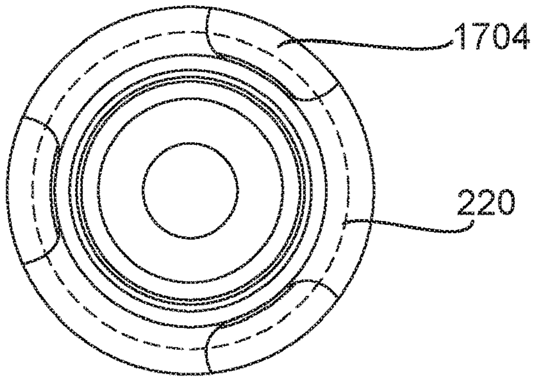

FIGS. 17*a*, 17*b*, and 17*c* show an example in which the guide hub 220 is provided with an external thread 1702. The external thread 1702 is a self-tapping thread arranged to bite or cut into the skull. This enables the hub to be rigidly secured to the skull. In addition, the threads cut by the external thread 1702 in the skull can later be used to retain other threaded components following removal of the guide hub 220. For example, a threaded bone plug may be inserted using the same hole to seal the hole in the skull. The external thread 1702 preferably has relatively deep grooves between the threads. Thereby, the external thread 1702 is configured to accommodate bone chippings produced when the external thread 1702 cuts into the skull. The minor diameter of the external thread 1702 may be smaller than the diameter of the drill hole into which the guide hub 220 is inserted by at least 0.2 mm, and preferably at least 0.4 mm. This allows the guide hub 220 to be inserted more easily, and may help in encouraging bone regrowth around the guide hub 220 due to the bone chippings in the external threads 1702. As shown in FIGS. 17*a*, 17*b*, and 17*c*, the guide hub 220 may also have a region above and/or below the external thread 1702 in which the outer diameter of the guide hub 220 matches the minor diameter of the external thread 1702, but in which no thread is provided. This provides further space to accommodate bone chippings that may be produced when the external thread 1702 cuts into the skull.

A proximal rim of the guide hub 220 may comprise hub engagement features for engagement with the hub insertion tool, which will be discussed in more detail below. The hub engagement features may comprise any suitable feature, for example grooves, protrusions, or notches. In the example of FIGS. 17*a*-17*c*, the hub engagement features comprise notches 1704 in the rim of the guide hub 220. Other examples of possible shapes include slots, holes, or castellations in the upper (proximal) surface of the guide hub. The hub engagement features allow a higher torque to be more easily and reliably applied to the guide hub 220 during insertion. This is particularly advantageous where the guide hub 220 comprises self-tapping threads, because it allows for the easy application of sufficient force for the threads to cut into the bone.

A further embodiment of the guide hub 220 may have an external thread that is inserted into a tapped hole, rather than being self-tapping. This would be a preferred solution when the guide hub 220 is made from a material that is not suitable for forming self-tapping thread, for example PEEK. In this instance the jig would have an extra tool to tap the hole to the desired depth.

Figure 2D:
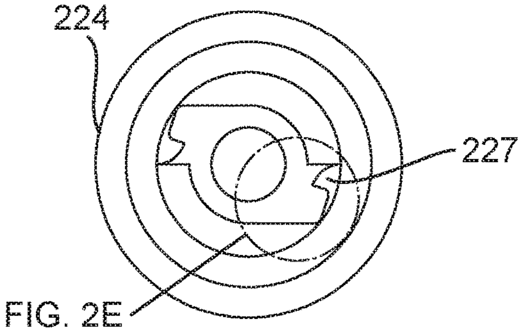
Figure 2E:
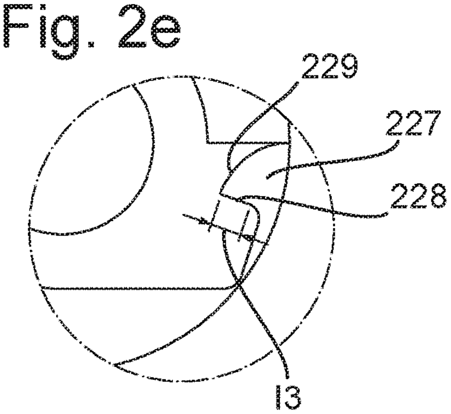
Figure 2F:
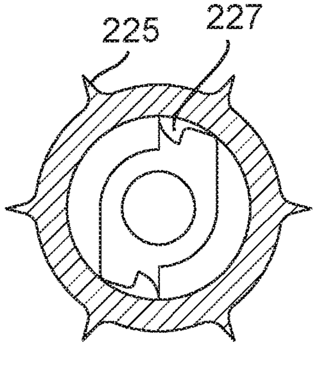

Referring now to FIGS. 2*d*-2*f*, the internal arrangement of a hub 220 is as follows. The through-bore 221 of the hub 220 comprises a double entry female thread 226 extending from the proximal end of the conical portion 222. The thread 226 used in the presently described example is an M4 thread and has a pitch of 2 mm and sweeps for half a revolution. The pitch may be adjusted for other threads used with hubs 220 of different dimensions.

As shown in FIG. 2*d*, each half revolution of thread 226 comprises a notch 227. A detail view of one of the notches 227 is shown in FIG. 2*e*. Each notch 227 is arranged to engage with a rib (not shown) on an apparatus to be inserted and locked into the hub 220. The notch 227 comprises a 0.08 $mm^2$ flat surface 228 of length (l3) of 0.2 mm, which extends radial to the through-bore 221 of the hub 220. This flat surface 228 engages with the rib on the apparatus to be inserted. For the example hub 220 shown and utilising an M4 thread 226, the notch 227 starts 0.34 mm from the start of the thread 226, which is 0.1 mm of lengthwise (L) translation into the hub 220 from the start of the thread 226. As shown in FIG. 2*e*, the notch 227 comprises a fillet 229 which is provided to allow the rib on an apparatus to be inserted to slide past the notch 227 and provide compression of the notch 227 and/or the rib on the apparatus. Once the rib has passed the fillet 229, it is securely engaged within the thread 226 and thus the apparatus is locked within the hub 220. FIG. 2*f* shows a cross-sectional view of the hub 220 of FIG. 2*b*, showing the broaching teeth 225 and the notch 227. Alternative locking screw thread arrangements such as of the Spiralock® type may be employed in the through bores 221 of hubs 220.

Figure 3A:
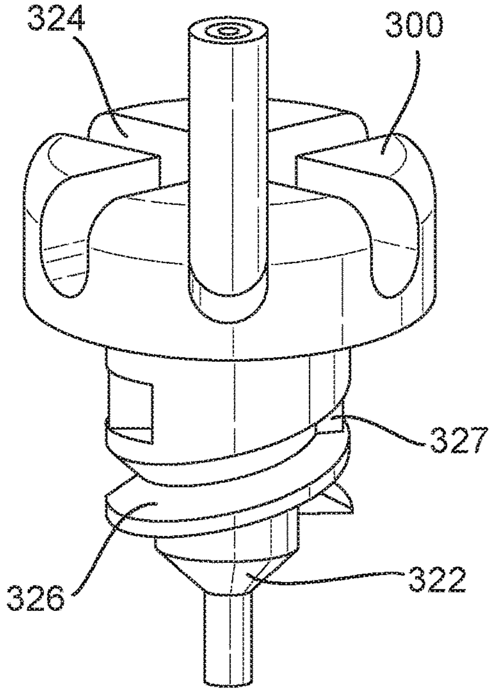
FIGS. 3*a* and 3*b* show a cap for use with the present invention.
Figure 3B:
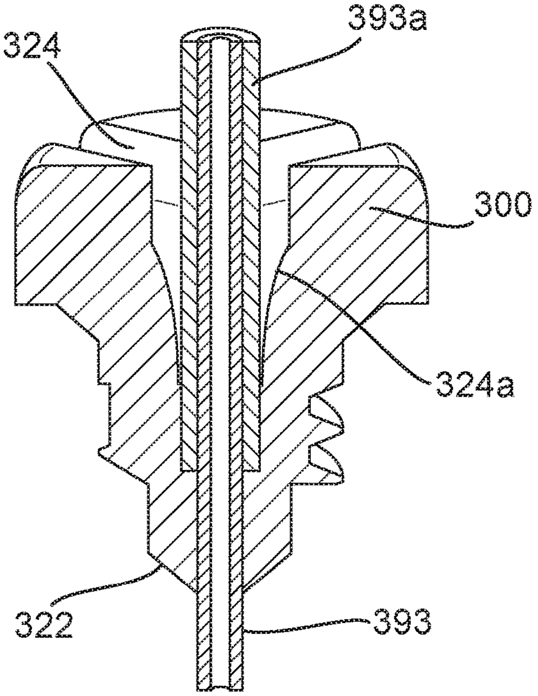

In an exemplary use of the hub 220, an exemplary cap 300 is described with reference to FIGS. 3*a* and 3*b*. The cap 300 is in the form of an overmould on a catheter or (in this example) a cannula 393 that may be made of PEEK or comprise PEEK. A cannula of PEEK has the advantage over the use of many other plastic materials in that it is robust, stiff and biocompatible and even with an external diameter in the region of 0.5 mm it can be delivered over several centimetres into brain tissue without deflecting from its trajectory. A further advantage of PEEK is that it can be readily cut and unlike fused silica, which is used in some CED cannulas, it is not brittle. PEEK can be made radio-opaque so that its position in brain tissue can be established with x-ray and CT imaging. The overmould acts as both a depth stop, and means of securing the catheter or cannula 393 to a guide hub. In this example the cannula 393 includes a protective sleeving 393*a* extending proximally from the cap 300. Prior to insertion of the cannula 393 through a guide hub 220 it is cut to a desired length (cap to cannula tip length) in a jig. The cap 300 has a plurality of radially outwards extending recesses (in the form of grooves) 324, on the upper surface. In this example six recesses 324 are provided. The radial recesses 324 allow engagement of a complementarily shaped end of a hollow screwdriver to turn the cap 300 within a hub 220, thereby screwing the cap 300 down the threads of the hub 220 and locking the cap 300 within the hub 220 by engagement of ribs 327 with the notch 227 of the hub 220. It is not essential that the guide hub 220 comprise the notch 227, and where the guide hub 220 does not include the notch 227, the cap 300 need not comprise the ribs 327. An example of a cap 300 without ribs is shown in FIGS. 18*a* to 18*d*. The hollow screwdriver may have a generally conventional hexalobular or "star drive" end for engaging the recesses 324. The end of the hollow screwdriver may attach by an interference fit to the radial recesses 324. This interference fit (or 'clip' fitting) is convenient as the cap 300 can be retained on the screwdriver whilst it is being put into position and screwed into a guide hub.

Figure 18A:
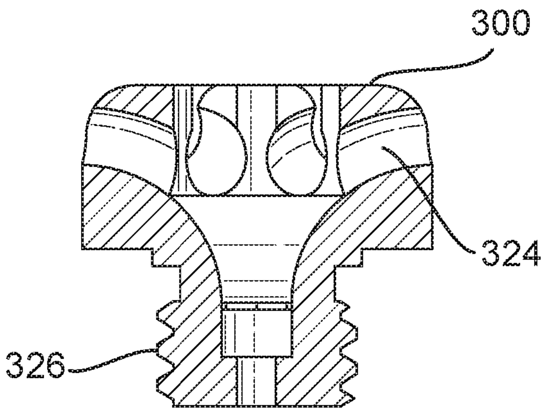
FIGS. 18*a* to 18*d* show a cap for use with the present invention.
Figure 18B:
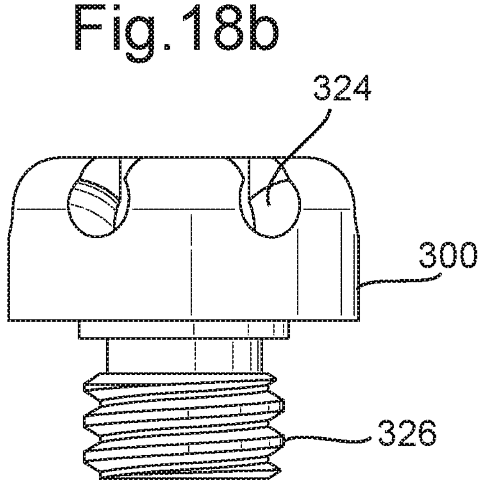
Figure 18C:
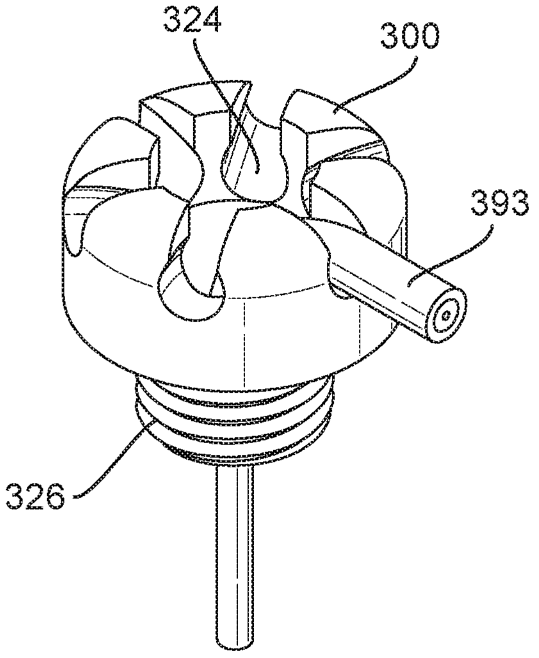
Figure 18D:
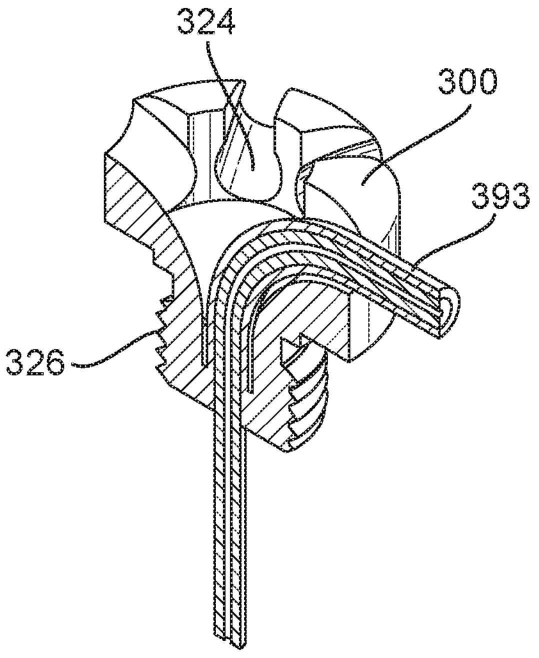

As also shown in FIGS. 18*c* and 18*d*, the radial recesses 324 also provide a means of retaining flexible cylindrical or tubular devices, such as cannula 393, after implantation into a patient when they are bent through 90° so as to provide a low profile, for example when they are chronically implanted under the scalp. The radial recesses follow a 90° radius of curvature (324*a*) out from the central axis of the cap. This radius defines and controls the bend radius of a device being fitted. Thus for devices with larger diameters the diameter of the radial groove will be greater. Typically larger diameter devices will require a larger radius of curvature, to avoid kinking or collapse of a tubing wall. These dimensions will therefore determine the size of the cap and guide hub where bending of a device is employed. In the example shown in FIG. 3*a* and FIG. 3*b* a sleeving 393*a* is made polyurethane and the cannula 393 of PEEK tubing, both of which are overmoulded with the cap 300. The sleeving 393*a* protects the fine PEEK cannula 393 and, being made of more compliant material than the cannula, facilitates its retention in an interference fit within recesses 324.

The cap 300 comprises a corresponding double male thread 326 to engage with the double entry female thread 226 of the hub 220 (FIG. 2*c*). The cap 300 further comprises a cap conical portion 322 at its distal end which is shaped and configured for sealing engagement with the conical portion 222 of a hub when the cap 300 and the hub 220 are locked together. The engagement of the cap 300 within the hub 220 and locking in sealing engagement will be described further later.

Figure 4A:
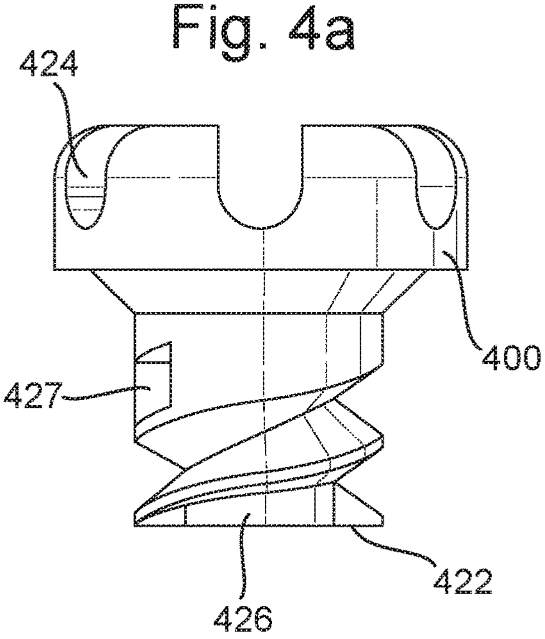
FIGS. 4*a* and 4*b* show an alternative cap.
Figure 4B:
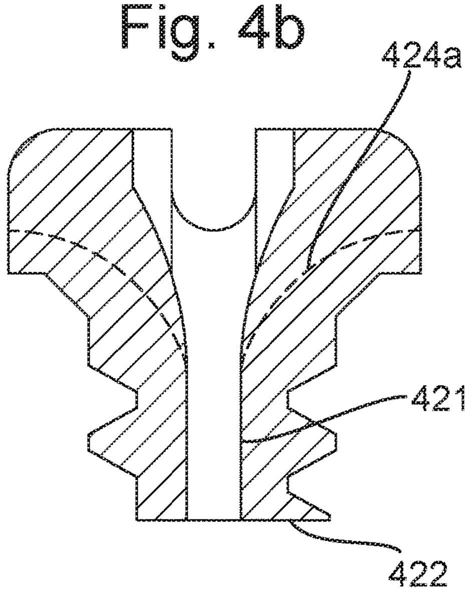

In a second example use of the hub 220, a second example of a cap 400 is used, as shown in FIGS. 4*a* and 4*b*. The cap 400 comprises a central through-bore 421 for passage of a device such as a, probe, electrode, catheter, cannula or other apparatus. The cap comprises a plurality of radial recesses 424 typically in the form of a hexalobular configuration on the upper surface. The radial recesses 424 allow engagement of a hollow screwdriver as discussed above with reference to the examples of FIGS. 3*a* and 3*b*. The cap 400 differs from the cap 300 in that the cap 400 is not an overmould on a device and does not comprise a cap conical portion at its distal end. Instead, the cap 400 comprises a cap through bore 421 and a cap flat portion 422 at its distal end which is configured to engage with a seal within an alternative hub 220, as will be described further later. The cap 400 also comprises a 90° radius of curvature (424*a*) for its radially extending recesses (grooves) 424.

A method of insertion of the hub 220 into the skull 500 of a patient is now provided with reference to FIGS. 5*a*-5*f*. Firstly, as shown in schematic FIG. 5*a*, brain imaging is performed to determine the location of a target 501 and a trajectory 502 with respect to a stereoguide datum 503. A stereotactic guidance system (not shown) is registered with respect to the target 501 and the trajectory 502. Registration of the stereotactic guidance system includes setting of the stereoguide datum 503 of the stereotactic guidance system at a predetermined distance from the target 501. Commercially available stereotactic guidance systems typically set their stereoguide datum 503 at around either 140 mm or 160 mm from the target 501. However, it will be understood that the chosen distance between the stereoguide datum 503 and the target 501 can be varied, for example when using a robotic arm to guide surgery, provided the distance used is known.

Imaging scans provide the surgeon with information relating to the skull thickness and location and arrangement of areas of interest within the brain. The known distance between the stereoguide datum 503 and the target 501 allows the surgeon to accurately plan surgery using instruments delivered using the stereotactic guidance system.

Datum Measuring and Tool Setting

Conveniently the setting of tools and devices for surgery when employing the guide hubs of the invention makes use of the jigs of the invention, as described in more detail and with respect to FIGS. 5 to 14 as discussed further below.

Figure 5A:
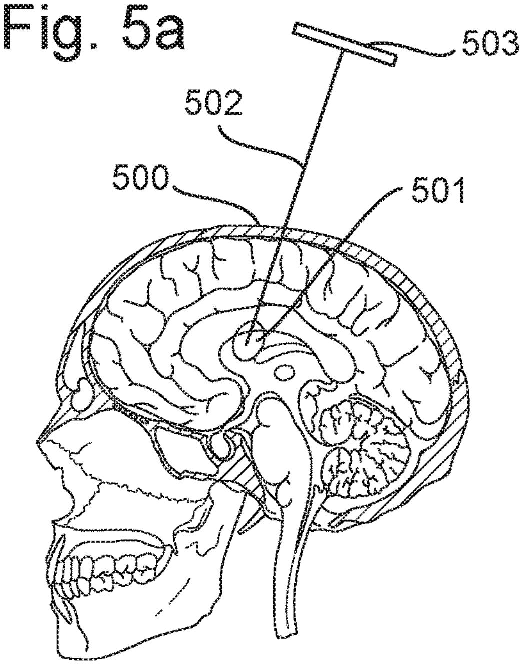
FIGS. 5*a*-5*k* show tools and a method used to install a hub in the skull of a patient and to provide a guide tube and catheter through the hub.
Figure 5B:
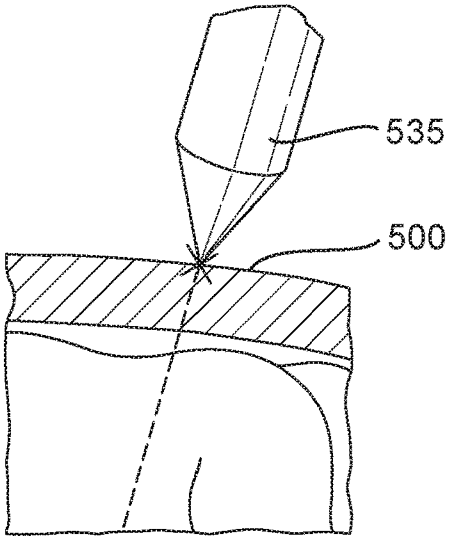
Figure 5C:
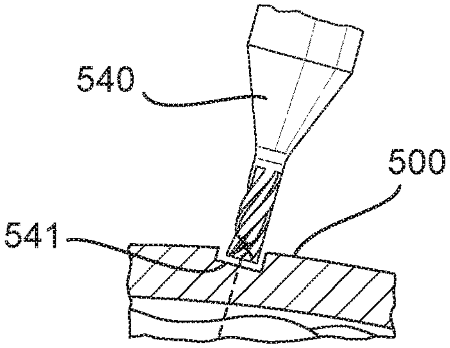

More generally, and as illustrated in FIG. 5*b*, a datum measuring tool 535 with a conical distal end is passed through the stereoguide that is set to the target trajectory. The distance from the datum on the stereoguide 503 to the surface of the skull 500 is measured, from which the penetration depth of the tools that are required to implant a guide hub into the skull are determined. To prepare the skull 500 for delivery of a hub 220, a facing tool 540 is mounted in the stereotactic guidance system and is brought into contact with the surface of the skull 500 along the trajectory 502, to create a flat surface 541 on the surface of the skull 500, as shown in FIG. 5*c*. This is to ensure that a fine pilot drill 550 which is subsequently delivered along the trajectory will not be deflected as it might be if engaging with the curved surface of the skull 500. The flat surface 541 provides a recess around 1 mm deep from the original skull top surface.

Figure 26:
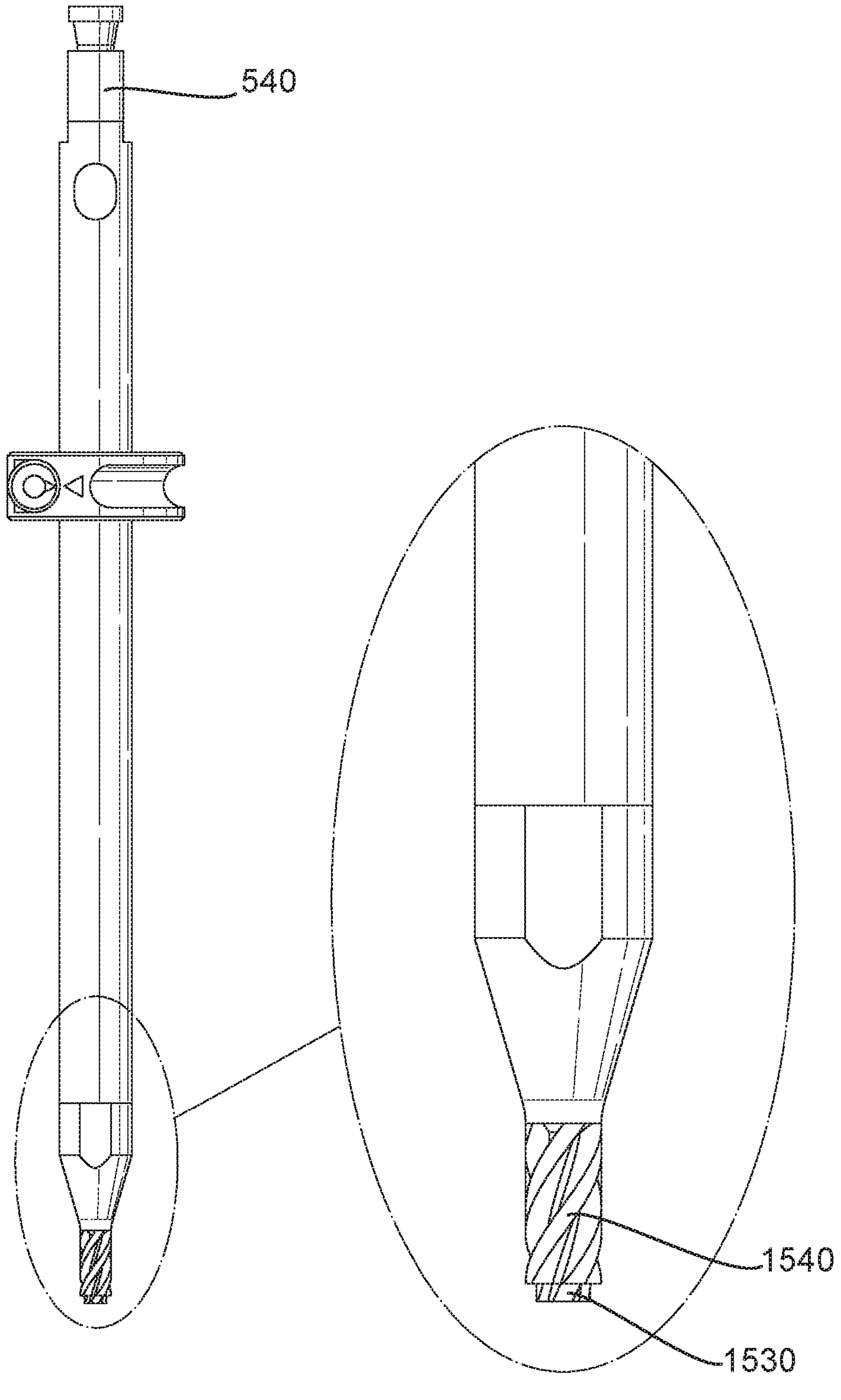
FIG. 26 shows a facing tool with a stepped distal profile.

As shown in FIG. 26, the facing tool 540 may have a stepped profile with a distal cylindrical cutter 1530 that has a smaller diameter than a more proximal cylindrical cutter 1540. This arrangement has particular advantage when creating a featured hole in a skull 500 that is acutely curved and thin, as for example in a child's skull. The smaller distal cutter 1530 will create a flat surface in the bone so that the pilot drill 550 will engage orthogonally with the bone surface to ensure that it drills concentrically, as discussed above. For example the distal cylindrical cutter 1530 may be between 0.5-1.5 mm deep, for example 1 mm deep, with a diameter of 2-4 mm, for example 3 mm. This steps up to the larger diameter proximal cylindrical cutter 1540, which is preferably larger than the diameter of the rim of the guide hub 220. For example, if the diameter of the guide hub's rim is 5 mm then the diameter of proximal cutting face may be 6 mm. The larger diameter flat surface created by the stepped facing tool ensures that the core drill that creates the profiled hole will engage with the bone orthogonal to the now flat surface and will not be deflected from its trajectory.

Figure 5D:
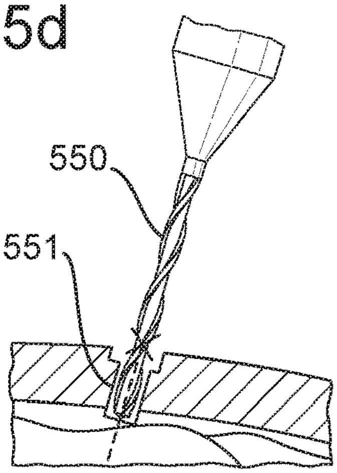
Figure 5E:
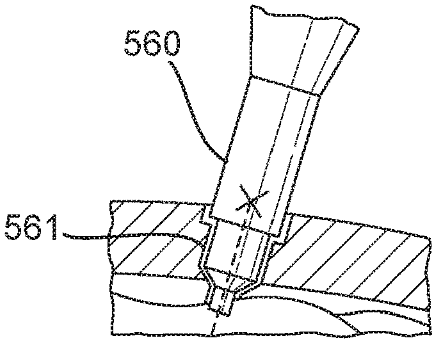

After making the flat surface 541, a pilot drill 550 is then used to penetrate the full thickness of the skull 500, thereby creating a pilot hole 551 as shown in FIG. 5*d*. A core drill 560 with a nib at its distal end is then inserted into the pilot hole 551 which guides it to form a profiled hole 561 in the skull 500, as shown in FIG. 5*e*, for allowing press fitting of an implantable hub 220 therewithin. The core drill 560 opens the pilot hole 551 and provides internal profiling to allow subsequent engagement of the hub 220 within the profiled hole 561 in a secure and low-profile manner.

Figure 5F:
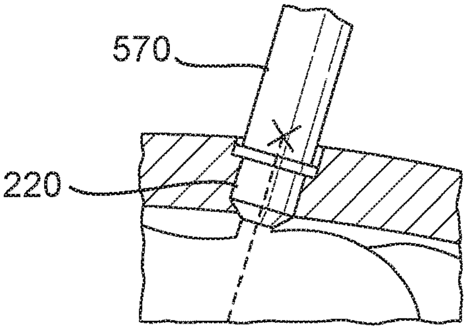
Figure 6B:
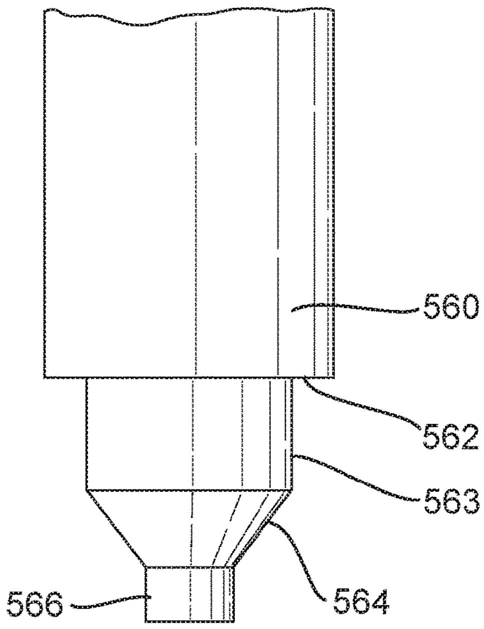
FIG. 6*b* shows a core drill.
Figure 6A:
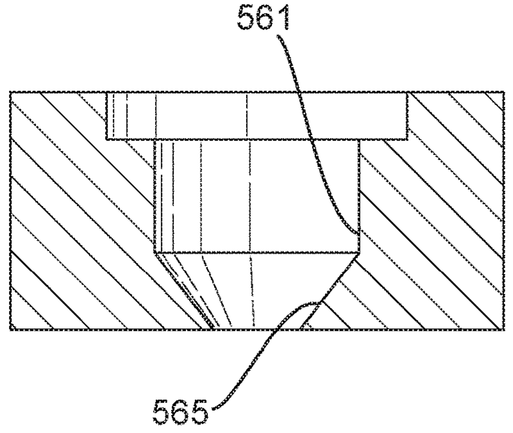
FIG. 6*a* shows a profiled hole.

A detailed view of the profiled hole 561 is shown in FIG. 6*a* and of the core drill 560 in FIG. 6*b*. Starting from the proximal end the core drill 560 comprises a step 562 which is configured to engage with the skull and create a 1 mm deep and 5 mm diameter recess into which the 0.5 mm high rim of the guide hub will be located. The core drill 560 further comprises a main body 563 which opens the pre-made pilot hole to around 4 mm in diameter for receiving a hub 220 (FIG. 5*f* discussed below). Additionally, the core drill 560 comprises a conical surface 564 towards its distal end which forms a shoulder 565 in the skull. The core drill 560 also comprises a nib 566 at its distal end for guiding the core drill 560 into the pilot hole. The profiled hole 561 formed as shown in FIG. 6*a* provides a press fit for an implantable hub 220.

The profiled hole 561 has been made along the desired trajectory 502 (FIG. 5*a*). Therefore when the hub 220 is inserted into the hole the passage through the hub 221 and central hole 223 are aligned along the trajectory.

Figure 27A:
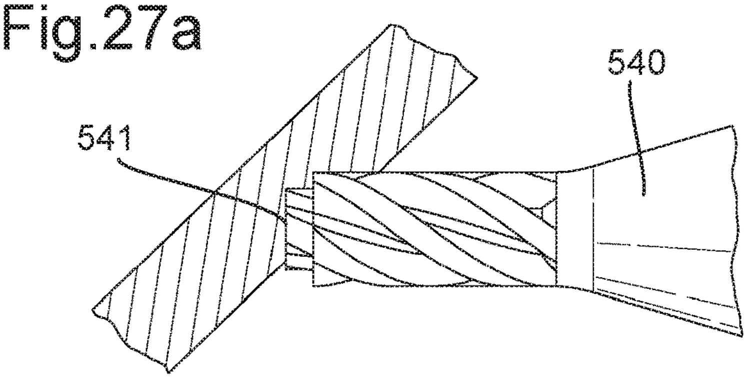
FIGS. 27*a* to 27*d* show the preparation of a highly curved skull surface for insertion of a guide hub using the facing tool of FIG. 26.
Figure 27B:
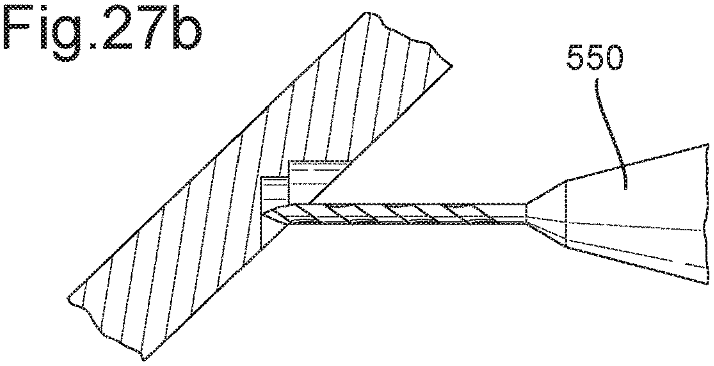
Figure 27C:
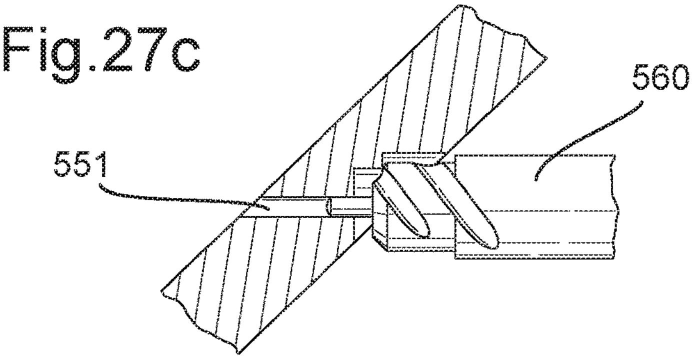
Figure 27D:
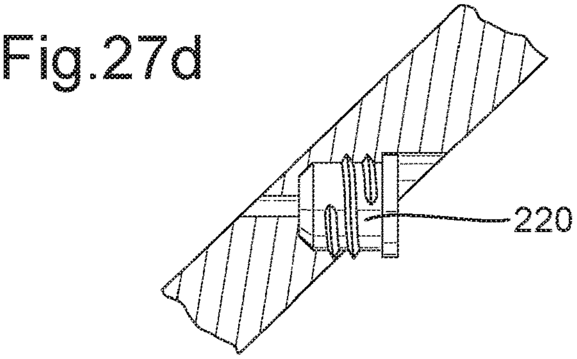

FIGS. 27*a*-27*d* show the equivalent process of preparing the skull for inserting the guide hub 220 using the stepped profile facing tool 540 in a highly curved skull surface. FIG. 27*a* is analogous to FIG. 5*c*, and shows the facing tool 540 being used to create the flat surface 541. FIG. 27*b* is analogous to FIG. 5*d*, and shows the pilot drill 550 being used to create the pilot hole 551. FIG. 27*c* is analogous to FIG. 5*e*, and shows the core drill 560 engaging with the pilot hole 541 to form the profiled hole 561. The guide hub 220 can then be inserted as shown in FIG. 27*d*. As seen in particular from FIGS. 27*c* and 27*d*, the stepped profile created by the facing tool 540 allows the core drill 560 and guide hub 220 to be brought into position on the skull surface without interfering with the highly curved skull surface in a manner which could cause deflection of the core drill 560 or improper insertion of the guide hub 220.

Figure 5H:
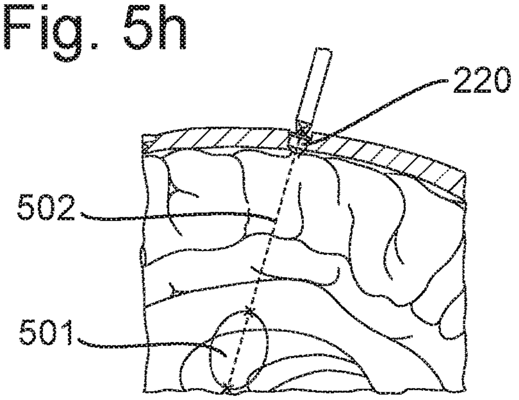
Figure 5G:
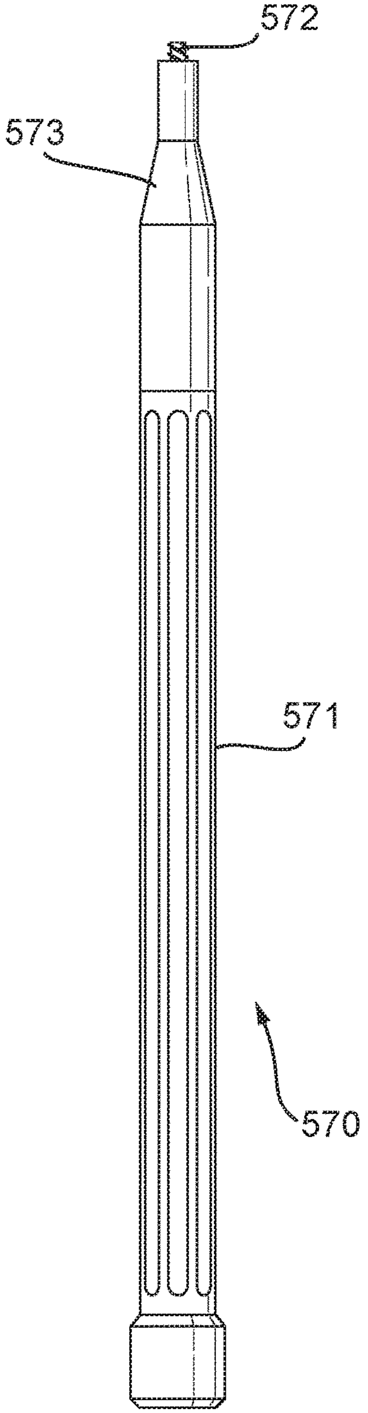
Figure 5I:
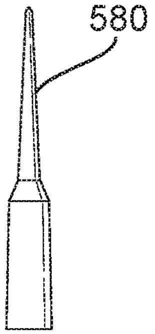
Figure 5J:
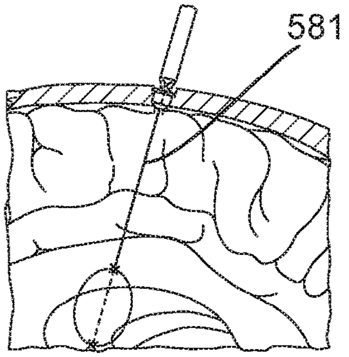

Referring now to FIGS. 5*f* and 5*g*, the insertion of a hub 220 into the profiled hole 561 in the skull 500 is explained. To insert the hub 220 into the profiled hole 561, the hub 220 is attached to an insertion tool 570 which is shown in FIG. 5*f* and in more detail in FIG. 5*g*. The insertion tool 570 comprises a shank 571 and a threaded distal end 572. The threaded distal end 572 comprises a male double entry thread which engages in the female thread 226 of the hub 220 by mating of the threads of the hub 220. In this example, the insertion tool 570 does not comprise a locking screw thread, thus allowing the insertion tool 570 to easily be removed from the hub 220 after the insertion tool 570 has delivered the hub 220 into the profiled hole 561.

The hub 220 can be aligned and accurately positioned in the profiled hole 561 of the skull 500 using the insertion tool 570. The shank 571 is dimensioned to be operable with a stereotactic guide. For example, insertion tool 570 comprises a shank of 150 mm length and 10 mm diameter. This allows the insertion tool 570 to be used with existing stereotactic guides and provides a sufficiently long insertion tool 570 to deliver the hub 220 to the profiled hole 561 using the stereotactic guide. The insertion tool 570 also comprises a chamfer 573 between the threaded distal end 572 and the shank 571. The chamfer 573 allows for a line of sight between the hub 220 and the medical professional when the hub 220 is brought into the profiled hole 561. The insertion tool 570 can be used to drive the hub 220 into the skull 500 with a force sufficient to enable broaching teeth or other external profile to bite or cut into the skull 500 and thereby secure the hub 220 into the skull 500 with the through-bore 221 co-axial with the trajectory 502 to the target 501. When an external thread or interference pattern is used instead of broaching teeth 225, the insertion tool 570 may have further features that are used to immobilise the tool with respect to the hub internal thread to allow an unscrewing action between the hub external thread and bone.

The insertion tool 570 can then be unscrewed from within the hub 220, leaving the hub 220 implanted in the profiled hole 561 in the skull 500.

Figure 19A:
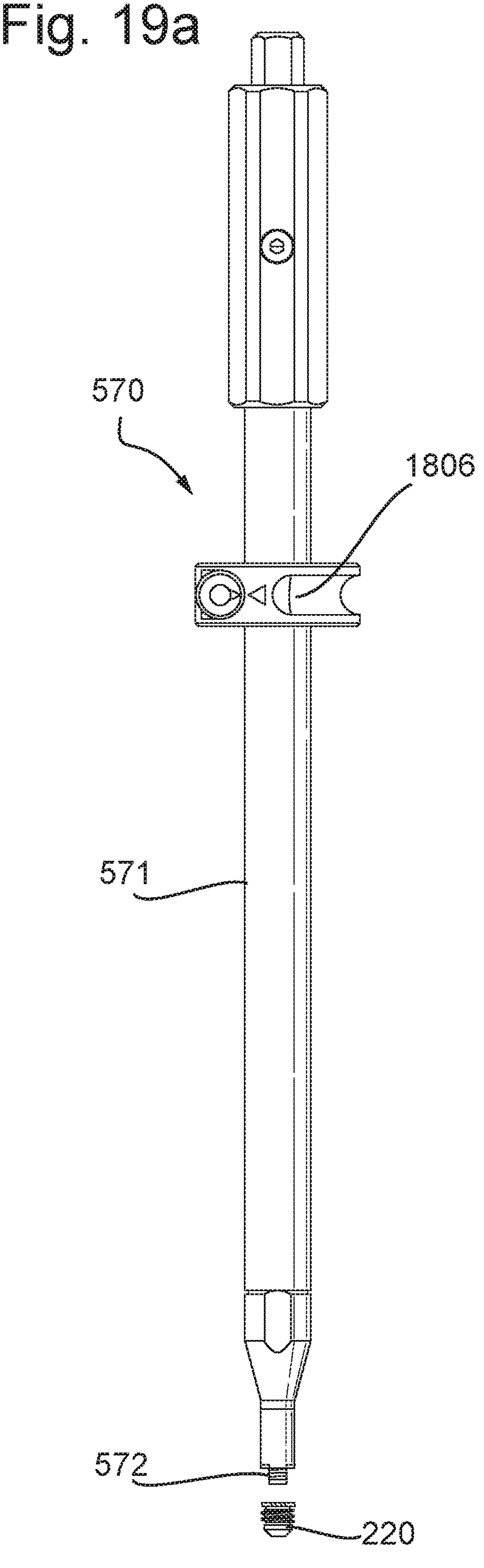
FIGS. 19*a* and 19*b* show an insertion tool having tool engagement features configured to engage hub engagement features on the guide device.
Figure 19B:
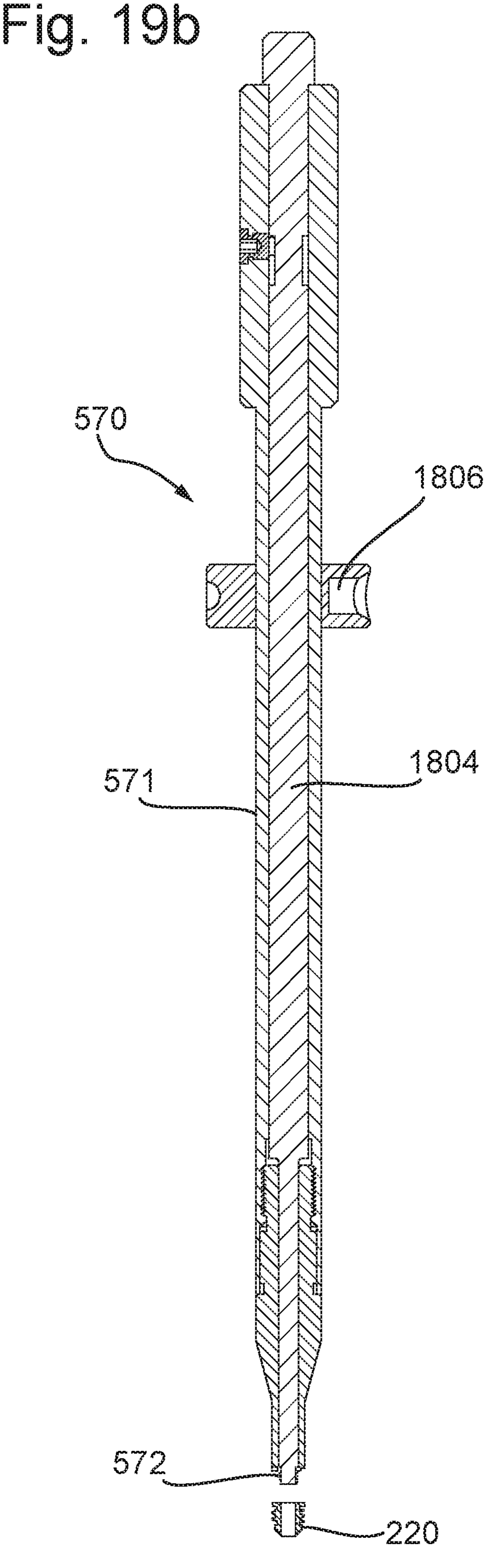
Figure 20A:
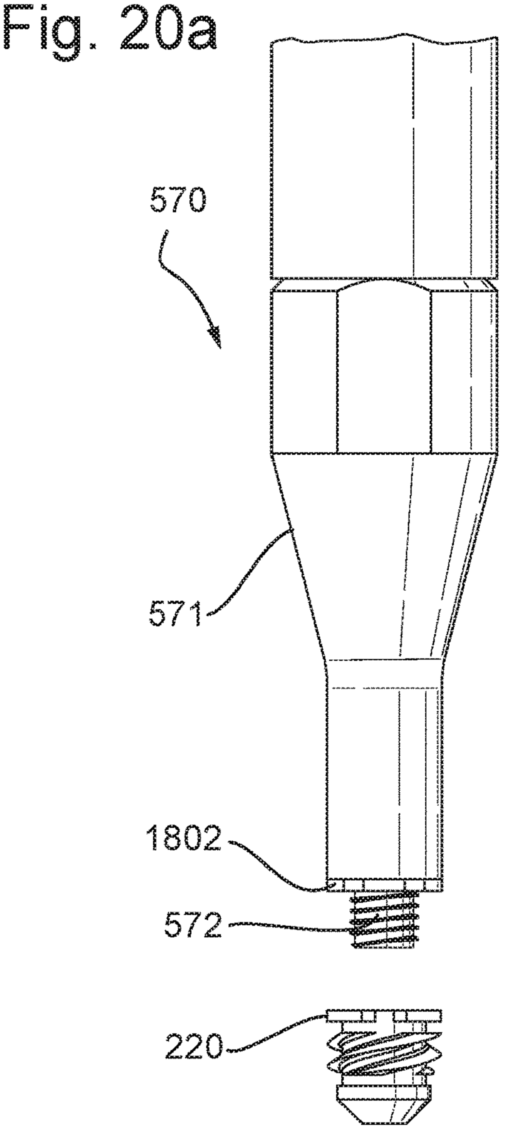
FIGS. 20*a* and 20*b* show a close-up view of a distal end of the insertion tool in FIG. 19.
Figure 20B:
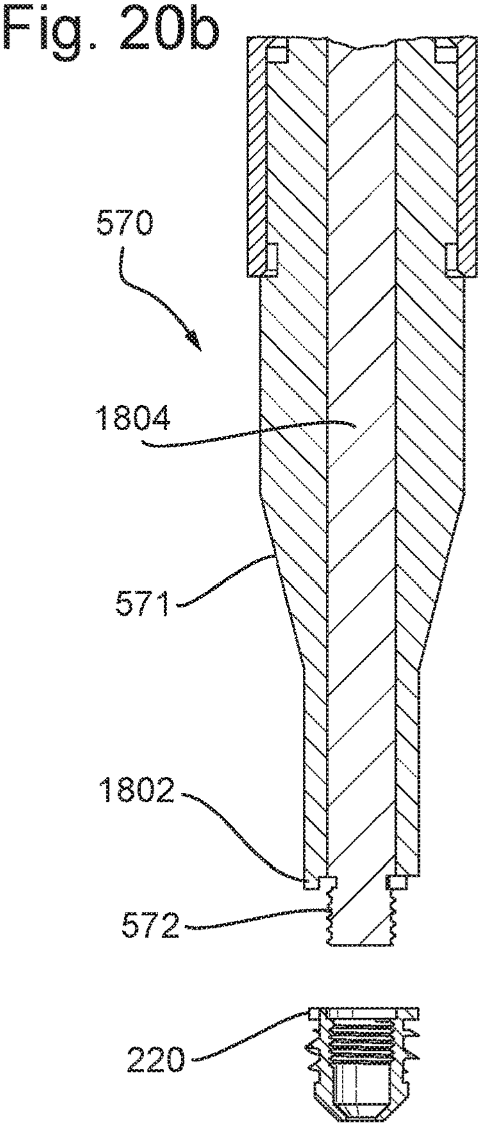

FIGS. 19*a* and 19*b* show another example of the insertion tool 570. A closer view of the distal end of the insertion tool 570 is shown in FIGS. 20*a* and 20*b*. As discussed above, the hub insertion tool 570 comprises a rod 1804 with a formation at its distal end for engaging with the second formation in the surgical guide hub 220. In this example, the insertion tool 570 is further configured to engage with the guide hub 220 via tool engagement features 1802. The tool engagement features 1802 may be configured to engage with hub engagement features 1704 on the guide hub 220. The insertion tool 570 may comprise a corresponding number of tool engagement features 1802 to match the number of hub engagement features 1704 on the guide hub 220. Preferably, a plurality of tool engagement features 1802 are provided spaced around an outer circumference of the insertion tool 570. For example, at least three, optionally at least four, tool engagement features 1802 may be provided. The tool engagement features 1802 may have any suitable shape. The shape of the tool engagement features 1802 may be chosen to correspond to the shape of the hub engagement features 1704. For example, the tool engagement features 1802 shown in FIG. 21 have the form of castellations and engage the notches that form the hub engagement features 1704. Where the hub engagement features 1802 comprise holes as mentioned above, the tool engagement features 1802 may comprise pins sized to fit into the holes. Preferably, the shapes of the tool engagement features 1802 and the hub engagement features 1704 are chosen such that the features can be easily engaged together and do not slip or easily become disengaged during use.

The formation at the distal end of the rod 1804, which in this example is the threaded distal end 572, may be configured to be movable relative to the shank 571 of the insertion tool 570. Preferably, the formation at the distal end of the rod 1804 is rotatable relative to the shank 571. The tool engagement feature 1802 may be provided on the shank 571 of the insertion tool 570, such that the shank 571 of the insertion tool 570 engages with the guide hub 220 via the tool engagement features 1802. This means that, following insertion of the guide hub 220 into the aperture, the insertion tool 570 can easily be disengaged from the guide hub 220 by moving (e.g. rotating) the formation at the distal end of the rod 1804 relative to the shank 571, without disturbing the placement of the guide hub 220 in the aperture. In addition, the engagement of the insertion tool 570 with the guide hub 220 via the tool engagement features 1802 can be used to apply a force to the guide hub 220 to insert the guide hub 220 into the aperture formed in the skull. This is particularly advantageous when the guide hub 220 comprises self-tapping threads, and a larger rotational force is required to cut into the skull as the guide hub 220 is inserted into the aperture.

Figure 21:
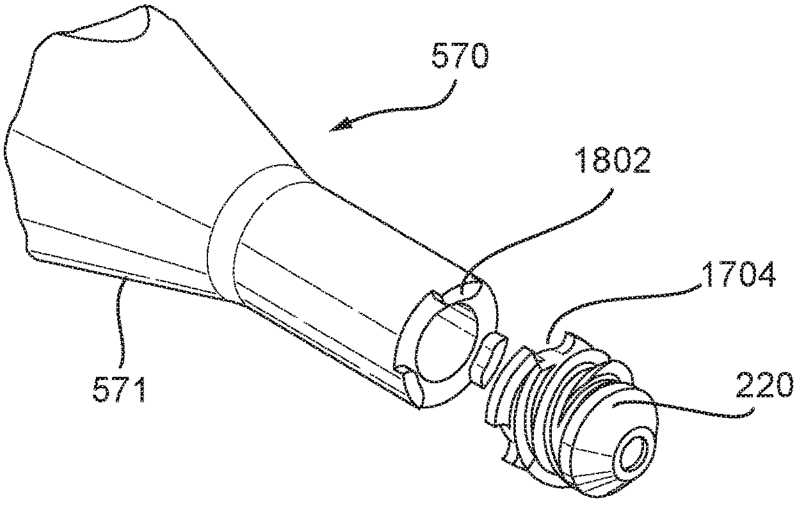
FIG. 21 is an isometric view of the distal end of the insertion tool of FIGS. 19 and 20.

FIG. 21 shows another view of the distal end of the insertion tool 570, illustrating the tool engagement features 1802 that engage with hub engagement features 1704 on the guide hub 220. As shown, the engagement of the tool engagement features 1802 with the hub engagement features 1704 allows for efficient application of rotational torque to the guide hub 220 for insertion of the guide hub 220 into the aperture.

The insertion tool 570 may also comprise a depth stop 1806 as shown in FIGS. 19*a* and 19*b*. The depth stop 1806 is analogous to the datum markers 537, 538, 539 discussed below in relation to other tools used in implanting the guide hub 220. The depth stop 1806 helps to prevent over-insertion of the guide hub 220 into the aperture. The depth stop 1806 may provide a visual and/or tactile indication of when the guide hub 220 has been inserted to the correct depth by engaging with the stereoguide datum 503. The depth stop 1806 may be movable with respect to the rod 1804 and/or shank 571 of the insertion tool 570. Before inserting the guide hub 220, the depth stop 1806 is set at the correct position along the insertion tool 570 such that the depth stop will engage the steroguide datum 503 when the guide hub 220 has been inserted to the correct depth in the aperture. The setting of the position of the depth stop 1806 may be carried out using the jigs of the invention.

Figure 22A:
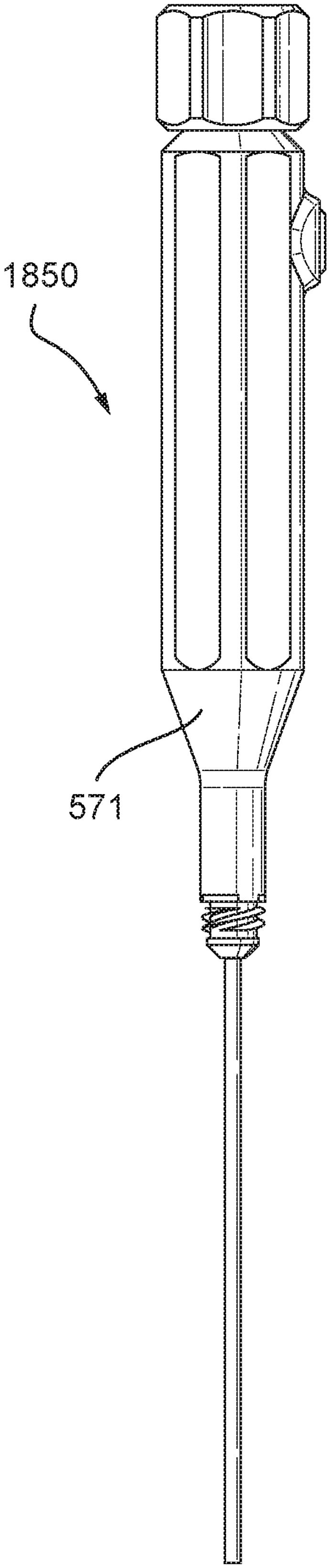
FIGS. 22*a* and 22*b* show a shortened tool for removing a guide device from a patient's skull.
Figure 22B:
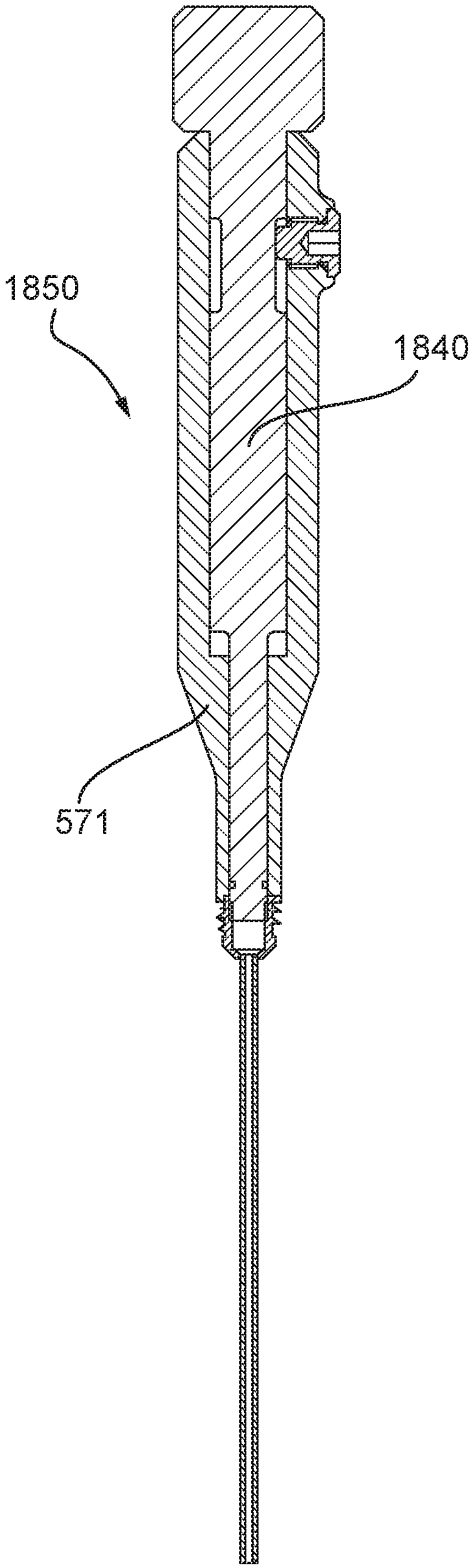

A system including the guide hub 220 may include a shortened tool 1850 as shown in FIGS. 22*a* and 22*b*. A distal end of the shortened tool 1850 is substantially similar to the distal end of the insertion tool 570 and comprises the threaded distal end 572 and/or the tool engagement features 1802. The shortened tool 1850 may comprise a shank 571 and rod 1804 that are movable relative to one another as for the insertion tool 570. However, the length of the shortened tool 1850 is less than the length of the insertion tool 570. This facilitates easier handling of the shortened tool 1850. The shortened tool 1850 may not comprise a depth stop 1806. This also facilitates easier handling of the shortened tool 1850. The shortened tool 1850 may be particularly suited for removal of the guide hub 220, where it is not necessary to control the axial position of the tool as accurately as during insertion of the guide hub 220. The shorter length and/or lack of the depth stop on the shortened tool 1850 also remove the need to handle the shortened tool 1850 using a stereoguide, which further simplifies use of the shortened tool 1850. The shortened tool 1850 may have a narrower diameter than the insertion tool 570. This gives the user a higher sensitivity to the force required to remove the guide hub 220, thereby improving control during the process of removing the guide hub 220.

The hub 220 can be located in the skull wholly within the recess 561 previously formed by the core drill. If desired the through bore of the hub 220 can be sealed, when not used for delivery of a device through the skull, by inserting a grub screw into the proximal end of the hub, which when fully inserted with e.g., an Alan key, has a proximal end that becomes flush with the proximal face of the guide hub.

Figure 5K:
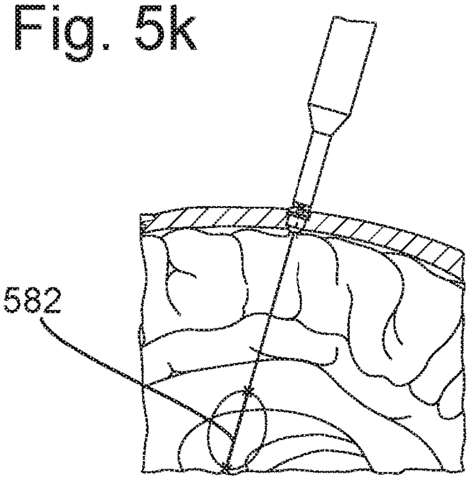

FIGS. 5*h*-5*k*, show an example use of the hub 220 when installed in the skull 500. As shown in FIG. 5*h*, the hub 220 is aligned along the trajectory 502, so that devices, and tools, such as cannulas, probes, electrodes or other neurosurgical apparatus provided through the hub 220 will also be directed along the trajectory 502 towards the target 501. In an example of the delivery of such apparatus, a track may be made through the brain tissue between the hub 220 and the target 501 by use of a track forming device 580 shown in FIG. 5*i*. In some procedures, a guide tube 581 may be inserted along the track formed by the track forming device 580. The guide tube 581 can be delivered through the through-bore of the hub 220 and may comprise a conical enlarged diameter proximal end which can seat against and seal against the conical portion 222 of a hub 220. As shown in FIG. 5*k*, a cannula 582 may then be inserted through the guide tube 581 to reach the target 501. In some examples, a device may be delivered through the hub 220 without the use of the guide tube 581. The device may be locked into the guide hub 220 in a similar fashion to the cannula 393 discussed above by providing the device with its own screw threaded portion for engaging with the screw thread within a hub 220 (FIGS. 2 to 4). The screw threaded portion may act as a stop to indicate the intended position (depth into the brain) to which the device should be inserted, and may prevent the device being inserted beyond its intended depth. The screw threaded portion may be configured to rotate independently of the rest of the device, to avoid coiling of the wire/tube of the device as the threaded portion is screwed into place. This could be achieved, for example, using one or more circumferential grooves with which corresponding protrusions on the threaded portion engage.

Figure 7:
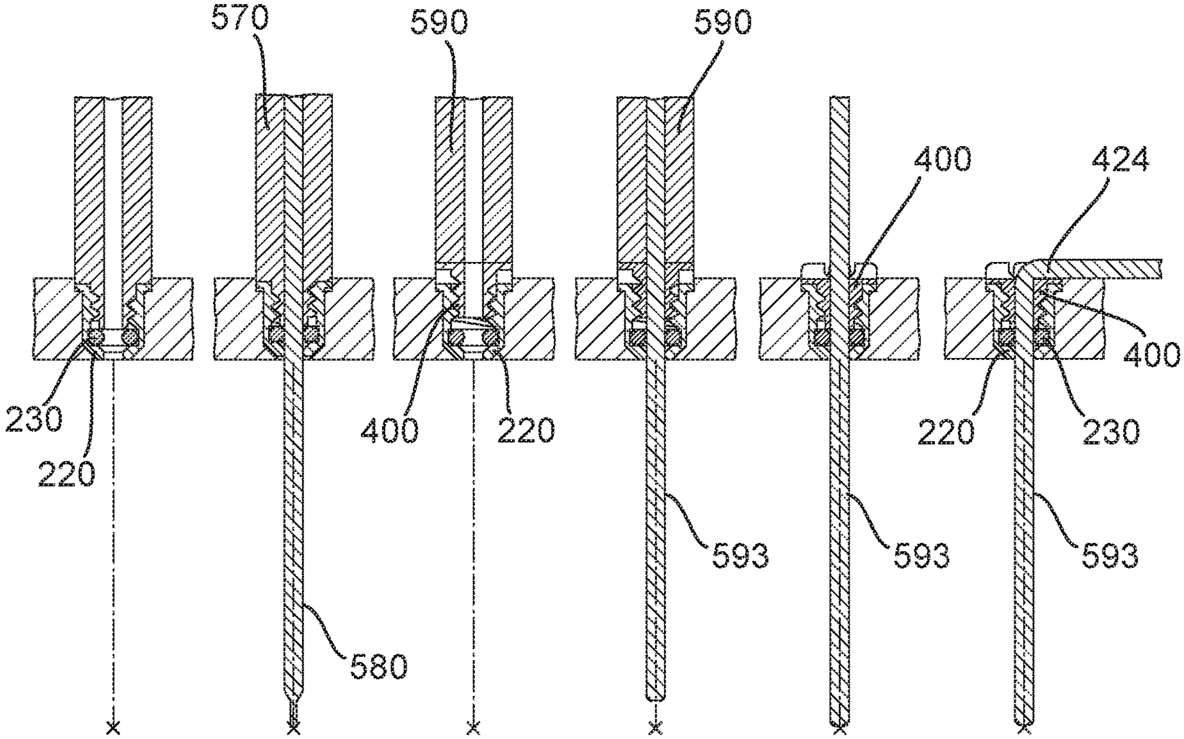
FIG. 7 shows a method of installing a cap within a hub in the skull of a patient and subsequently installing a cannula or a DBS electrode lead in the brain of a patient.

FIG. 7 shows an example of insertion of a device through the hub 220 in sequence of schematic views from left to right. In this example the device 593 is a Deep Brain Stimulation (DBS) electrode. The hub 220 is firstly inserted into a profiled hole in the skull as previously described and the track forming tool 580, mounted in an insertion tool, is then passed through the hub 220 to create a track along the desired trajectory in the brain. The insertion tool for the track forming tool may be the hub insertion tool 570 as shown here. In this example, the hub 220 comprises a seal 230 which is in a free non-compressed and non-sealing state as the tracking tool 580 is passed through the hub 220. The tracking tool 580 is then removed and a cap 400 is brought into the hub 220. Since the presently described example hub 220 comprises a seal 230 in the form of an O-ring seal, the cap 400 comprises a cap flat portion 422 as in the example shown in FIGS. 4*a* and 4*b*, rather than a cap conical portion 322 as shown in FIGS. 3*a* and 3*b*.

Use of a hollow screwdriver 590 and through-bore of the cap 400 allow delivery of the device 593 through both the hollow screwdriver 590 and the cap 400. Turning the cap 400 with the hollow screwdriver 590 moves the cap 400 downwards and into engagement with the seal 230, thus compressing the seal 230 axially and thereby expanding it radially. The seal 230 then provides a fluid, gas and bacterial seal between the hub 220 and the cap 400 that securely grips the device 593 passing through hub 220.

Figure 8:
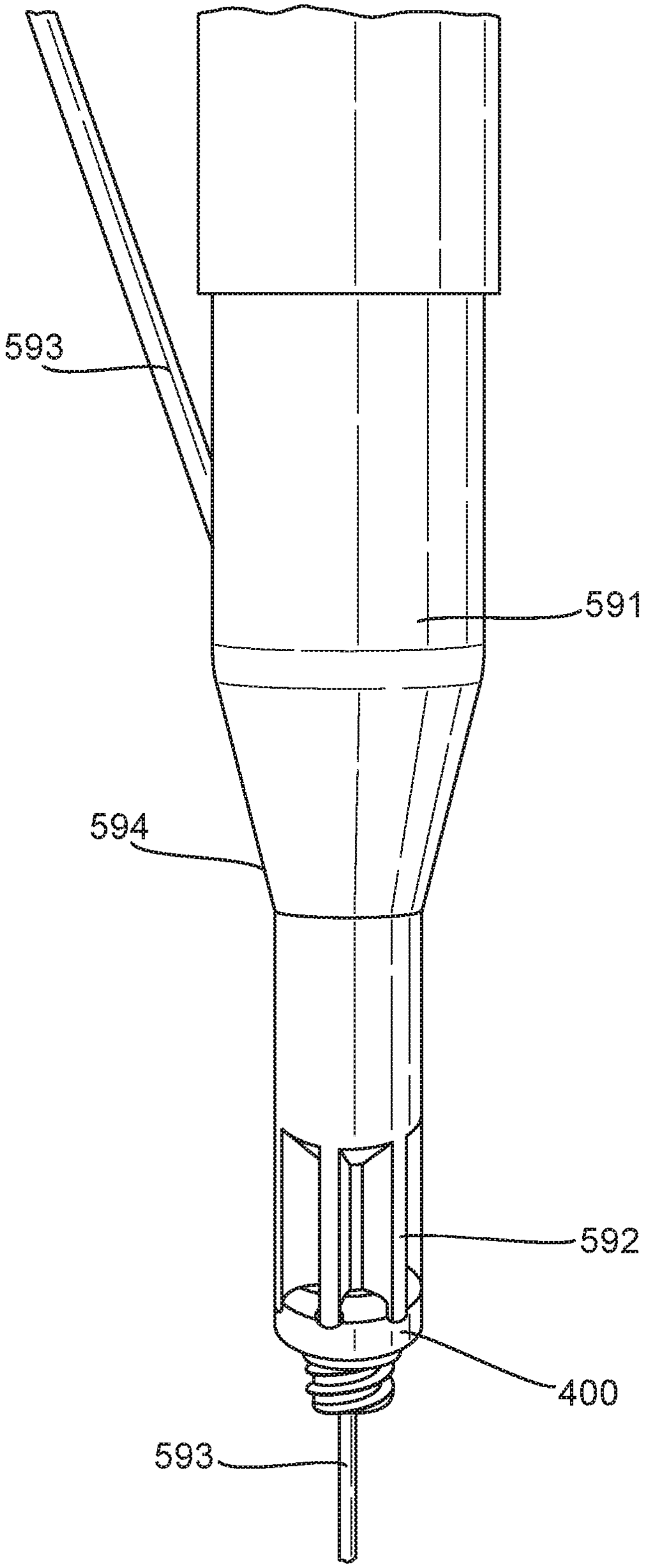
FIG. 8 shows a screwdriver comprising an axially extending slot at its distal (head) end.

In the example of FIG. 7, the hollow screwdriver 590 is configured such that a device 593 enters its proximal end and exits the screwdriver 590 from the distal end. Advantageously such a screwdriver is provided with an air vent hole at its distal end so that air is easily vented as the DBS electrode is inserted into the brain. An alternative arrangement is shown in FIG. 8. Alternative screwdriver 591 has a hexalobular formation 592 at its distal end, but with one lobe of the six absent (see also FIGS. 16*a* and 16*b* discussed below). The hexalobular formation engages the recesses of the cap 400 with an interference fit to attach the screwdriver temporarily to the cap. A cannula 593 extends through the cap 400. The screwdriver 591 comprises an axially extending slot 594 at its distal (head) end so that the cannula 593 can exit out the side of the screwdriver 591. This arrangement can allow a device with a part on its proximal end that will not pass through the bore of the hollow screwdriver to be delivered into a guide hub. For example, the end of cannula 593 may have a fluidic connector for joining to a fluid supply line which has a diameter larger than the bore of the screwdriver. The slot 594 in screwdriver 591 also provides a convenient air vent. In some examples screwdriver 591 may be hollow along its length and so able to be used for delivery of devices as shown in ether FIG. 7 or FIG. 8.

Figure 23A:
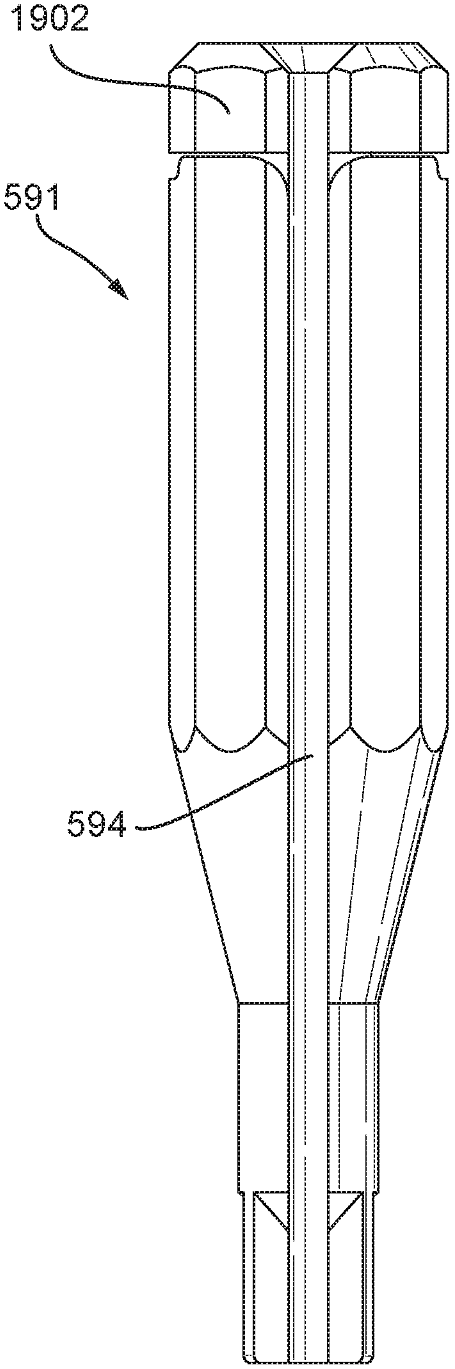
FIGS. 23*a* and 23*b* show a screwdriver comprising an axially extending slot along its entire length.
Figure 23B:
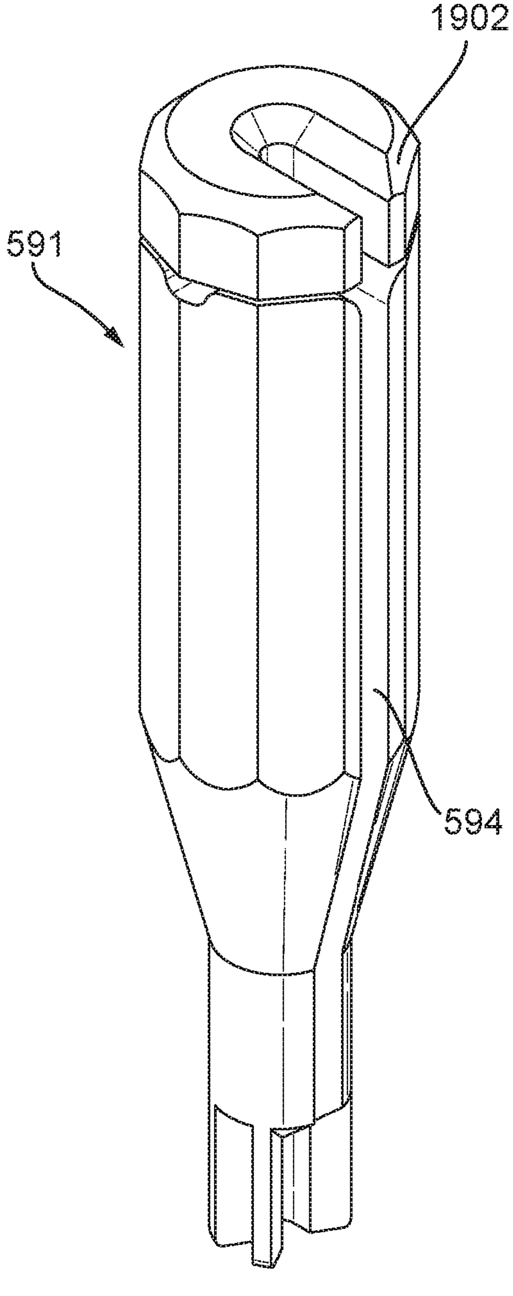
Figure 24:
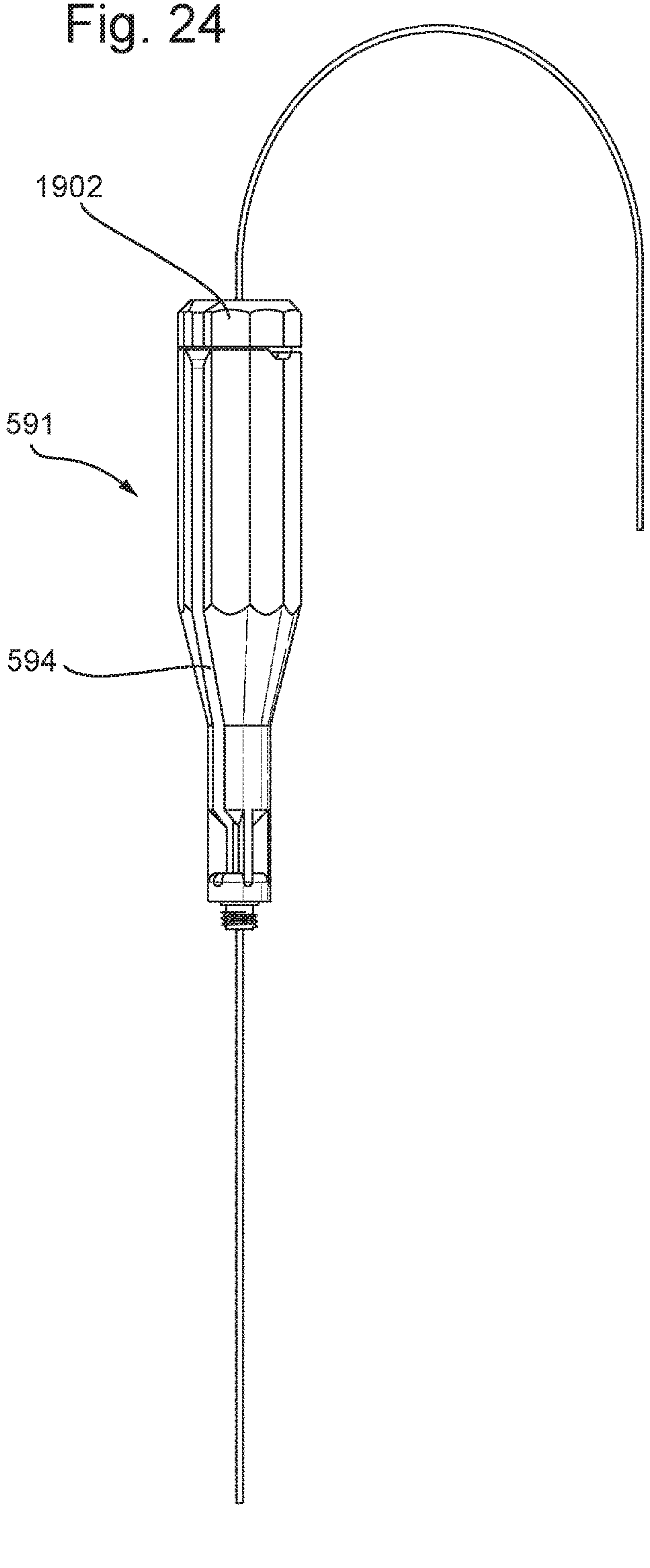
FIG. 24 shows the screwdriver with a device positioned along its hollow central axis.

As shown in FIGS. 23*a* and 23*b*, the axially extending slot 594 may extend to the extreme proximal end of the screwdriver tool, such that the slot 594 extends along the entire length of the screwdriver 591 from the distal end to the proximal end. As described in relation to FIG. 8 above, this allows a device 593 with a part on its proximal end that will not pass through the bore of the hollow screwdriver 591 to be delivered into a guide hub 220 using the hollow screwdriver 591. However, having the slot 594 extend along the entire length of the screwdriver 591 allows the device 593 to be positioned approximately along the axis of the screwdriver 591 through the bore of the screwdriver 591. This is illustrated in FIG. 24, which shows the screwdriver with a device positioned along its axis ready for delivery. This allows the hollow screwdriver 591 to rotate around the device 593, thereby preventing the device 593 becoming tangled or coiled around the screwdriver 591 as the screwdriver 591 is rotated to deliver the device 593.

The screwdriver 590 or 591 may further comprise a latch 1902, for example in the form of a rotating collar or rotating disc as shown in FIGS. 23*a* and 23*b*. The latch 1902 may be configured to reversibly block the slot 594 (for example by blocking entry to the slot 594 from a radial direction) along at least part of the length of the slot 594. The latch 1902 is preferably provided at or near to the proximal end of the screwdriver 591. The latch 1902 may act to hold the device 593 within the hollow bore of the screwdriver 590 and prevent it from falling out of the screwdriver 591 again via the slot 594. This can reduce the chance of the device 593 becoming coiled or tangled around the screwdriver 591 as the device 593 is delivered or removed from the guide hub 220.

Referring back to FIG. 7, after locking of the cap 400 in the hub 220, the device 593 can be bent into one of the radially extending recesses 424 of cap 400 to provide a low-profile and secure attachment. At the end of the process shown in FIG. 7, the inserted apparatus has been locked within the hub 220 and a gas, fluid and bacterial seal has been created. The device shown in FIG. 7 is a DBS electrode, however such methods can also be employed, with other devices such as catheters or cannulas.

Removal of a device from the patient can be straightforward. Referring again to the sequence of FIG. 7, but starting from the right hand view, the device can be removed from the recess 424, and a hollow screwdriver of one of the types 590 or 591 inserted over the device to engage in the recesses 424. Advantageously the screwdriver is of the type 591 with a side slot 594. The screwdriver 591 can be placed onto the cap with the device 593 accepted in slot 594. The screwdriver can then unscrew the cap 400 to release the seal and in this way the cap 400 and apparatus can then be easily removed after use.

The implanted guide hub 220 can facilitate repeated access to intracranial targets without the requirement for further stereotactic surgery. To replace a faulty electrode or a ventricular catheter for example, the device is removed as described above and the cap 400 is screwed back into the hub 220 without compressing the O-ring. This aligns the hollow screwdriver 590 along the axis of the trajectory 502 to the target 501. The distance from the hub datum HD to the target 501 is known and will have been recorded in the surgical notes (FIGS. 2*b* and 5*a*). The hub datum HD to target 501 distance is added to the length of the proximal end of the screwdriver 590 to the hub datum HD distance and a depth-stop is secured to the replacement device this same distance from its distal end. The replacement device is now delivered down the hollow screwdriver 590, cap 400 and guide hub 220 to its target 501 which is reached when the depth stop engages with the proximal end of the screwdriver 590. The screwdriver 590 is rotated to lock the device in the guide hub 220, the depth-stop is then removed followed by the screwdriver 590, leaving the replacement device in situ, with its distal end at the target.

Approximately one third of Intraventricular catheters implanted for the treatment of hydrocephalus will become blocked and need replacing every 10 years. Re-accessing the ventricle for replacement of a catheter can be technically difficult. Advantageously the guide hub may be employed to accurately place and secure a ventricular catheter and simplify its accurate replacement should it become blocked. In such an example, removal of a blocked catheter is achieved by attaching a screwdriver 591 to the cap 400 and unscrewing it. This releases the catheter which can then be withdrawn through the side slot in the distal end of the screwdriver 591. A new catheter is now delivered through the hollow screwdriver 591 and through the cap 400 and hub 220 to the same depth as the original catheter. The new catheter is secured by re locking the cap 400 into the hub 220.

Re-access to the same target 501 for repeated treatment without the need for further stereotactic surgery may also be achieved with the guide hub 220 by replacing a device such as a lesioning electrode, catheter or cannula with a plastic stylet of the same length. The stylet, fixed in the hub 220 by a proximal threaded cap will maintain patency of the track and facilitate re-access to the target 501 days, months or years later. Alternatively, following removal of a device a blind cap (not shown but a cap 300, 400 without a central through-bore), may be located in the hub 220 and secured and sealed in the same manner as previously described with reference to either FIG. 3*a*, 3*b* or 4*a*, 4*b* to provide safe sealing of the hub 220 to prevent infection or loss of fluid from within the head. Alternatively, a grub screw cap, with the same male thread as the cap 300, 400 may be screwed into hub 220 with an allen key such that its proximal face becomes level with the proximal surface of the hub. This will seal to a hub 220 providing a low-profile, reaccessible alternative to other somewhat bulkier caps.

Referring again to FIGS. 5 and 7, re-access to the intracranial target 501 can be achieved by removing the blind cap, screwing a guide hub insertion tool 570 into the hub 220 which thereby becomes aligned and fixed coaxial with the trajectory 502 to the target 501. A probe is then inserted down the hollow guide tube insertion tool 570 to the target which is at a known distance from the hub datum HD (FIG. 2*b*). The probe is removed leaving a track to the target 501 and the guide hub insertion tool 570 is now removed. The cap 400 is attached to the screwdriver 590 and screwed into the hub 220 without compressing the O-ring. As described above the device is now inserted through the hollow screwdriver 590 or 591 to the target and locked in position.

Using conventional methods of drilling on the surface of the skull to form a profiled hole and deliver a device typically requires many measurements to be taken, particularly when multiple different pieces of equipment are used to form the hole for the introduction of a hub. The risk of human error across the entire surgical procedure increases when repeated procedures are required, as the calculations of each step must be performed again during the repeated procedure.

Jigs are now described which assist in setting tools for neurosurgery and cutting the length of implantable devices with reduced calculation and adjustment required.

Figure 9:
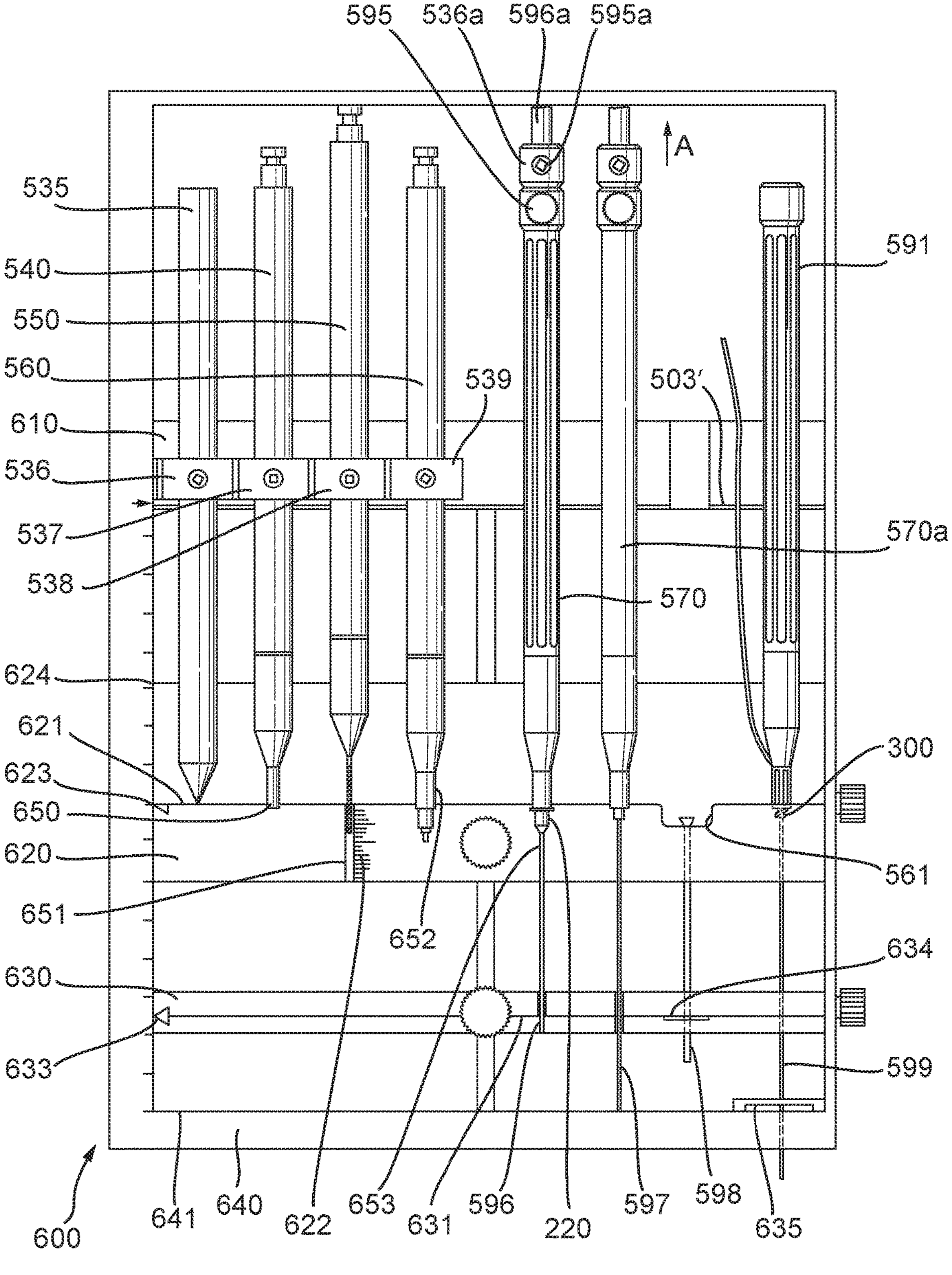
FIG. 9 shows a jig in accordance with the present invention.

A jig 600 is shown in FIG. 9. The jig 600 is for setting the depth of insertion of multiple neurosurgical tools and devices into the skull or brain of a patient during neurosurgery. The jig 600 can be used for setting the tools and devices used in surgical procedures such as those shown in FIGS. 5*a* to 5*k* and described above.

The jig 600 comprises an open rectangular frame and has an upper cross bar that provides a tool aligning device 610 and has a representative datum 503' that represents the stereoguide datum 503 of FIG. 5*a*. The jig 600 has a lower crossbar 640 with a target datum 641 in the form of a surface that corresponds to the target 501 in a patient's brain shown in FIG. 5*a*. The tool aligning device 610 can be moved in parallel to the lower cross bar 640 and its position fixed with reference to the scale 624 so that distance between the representative datum 503' and the target datum 641 correspond to the stereoguide datum to target 501 distance of the stereotactic guidance system in use. For the commercially available Cosman-Roberts-Wells stereoguide the distance between the stereoguide datum and the target is set at 160 mm. For the Leksell® stereoguide the distance is set at 190 mm. When the jig 600 is used exclusively with a stereotactic guidance system with a fixed stereoguide datum to target distance, the jig 600 may be provided with a fixed relationship between the upper and lower cross bar 640 but otherwise the upper cross bar would preferably be adjustable relative to the lower cross bar 640. For example, the stereoguide datum to target distance may be varied by the operator for a specific target when the stereoguide is a surgical robot or when the stereotactic guidance system is an instrument guide on a moveable and lockable arm whose spatial relationship to a target in a patient's head, registered to volumetric images, is tracked using optical, ultrasonic or electromagnetic sensors. In these latter circumstances the stereoguide datum to target distance defined in the planning software is set in the jig 600 for that individual target.

The tool aligning device 610 is provided with slots or grooves to receive and align generally elongate tools and tool stops and direct their distal ends orthogonally towards a moveable reference guide 620 that is parallel to the tool aligning device 610. The reference guide 620 is in a form of a bar parallel to the tool aligning device 610 and is moveable relative to the tool aligning device 610 whilst retaining the parallel relationship. The means for maintaining a parallel relationship are described hereafter and with reference to FIGS. 11 to 13. The reference beam 620 has an upper datum surface 621 that represents the skull surface 500 when carrying out procedures such as illustrated in FIGS. 5*a* to 5*k*. The reference guide 620 can be moved to set a baseline length from the datum line 503' of the tool aligning device 610 to the datum surface 621.

The jig 600 may further comprise a moveable cutting or depth measuring guide 630 having a surface 631 to be located at selected distances from the target datum 641 as will be explained in more detail later. The moveable surface 630 is in the form of a bar parallel to and positioned below the reference guide 620 and above the lower crossbar 640 providing the target datum 641. A further device cutting surface 635 may be provided at the target datum 641.

As will be shown in other examples, the jig 600 may be laid at an angle, for example 45 degrees to the horizontal. This can be convenient in allowing tools placed on the jig 600 (e.g. located in the aligning device 610) to move into place under gravity.

The use of the jig 600 to prepare tools to make a profiled hole 561 in a skull, such as illustrated in FIGS. 5*a* to 5*d*, is now described.

A stereoguide is aligned to the planned trajectory 502 directed to the target 501 in the patient's brain. After making an incision to expose the surface of the skull 500 a datum measurement tool 535 in the form of a rod is held in the stereoguide and brought into contact with the skull of the patient (FIG. 5*b*). The baseline length from stereoguide datum 503 to the skull 500 can be marked on the tool or measured. Conveniently, a datum marker 536 is clamped to the tool at the stereoguide to fix the start of the baseline length. The datum marker 536 takes the form of a collar that fits about the tool 535 and clamps to it by means of a grub screw. The datum measurement tool 535 is then transferred to the jig 600 and is held in the tool aligning device 610 with the first tool datum marker 536 sitting in a slot of the aligning device 610 as shown in FIG. 9. The bottom of the slot is part of the representative datum 503'.

The reference guide 620 is then moved up so that the datum surface 621 of the reference guide 620 comes into contact with the distal end of the datum measurement tool 535 and the reference guide 620 is then locked or held in position. Thus, the distance from stereoguide datum 503 to skull surface 500 on the patient is established on the jig 600 as the baseline distance from representative datum 503' to datum surface 621.

Alternatively the baseline length from 503' to 621 in the jig 600 can be set by using a measured distance obtained using the datum measurement tool 535 or by any other means such as a laser rangefinder, other measuring tool, or imaging technique employed with a robot arm or stereotactic frame.

The reference guide 620 has multiple offsets or channels through from datum surface 621 which allow setting different lengths for surgical tools and devices with different functions, as will now be described.

For preparing a hole in the skull and inserting a guide hub 220 the sequence may be as follows. A first offset 650 in the form of a depression in the datum surface 621 is for setting the facing tool 540. A second offset 651 including a channel through the reference guide 620 is for setting the pilot drill 550. A third offset 652 is for setting the core drill 560. Each offset 650, 651, 652 provides a distance from the datum surface 621 corresponding to a distance beyond the skull surface on the patient to which each tool should extend when carrying out its task during surgery. Therefore, the offsets 650, 651, 652 in the reference guide 620 to allow the setting of different tools following only one initial measurement, i.e. establishing the baseline length.

To set the length of the facing tool 540 from representative datum 503', the facing tool 540 is located in the tool aligning device 610 and its distal end brought to the first offset 650. The length of the facing tool 540 from representative datum 503' to distal end is set by clamping a tool datum marker 537 to the tool 540. The tool 540 can then be used with the stereoguide to cut a flat face on the skull, as shown in FIG. 5*c*, boring down to exactly the desired depth.

In a similar fashion, the pilot drill 550 is brought to the second offset 651 and the length required (to bore through the skull but avoid entering the brain—FIG. 5*d*) set by clamping a third tool datum marker 538 to the pilot drill 550 after advancing the pilot drill to the depth required to penetrate the skull, which has been determined from the brain imaging scans and can be set precisely using a scale 622 on the moveable reference guide 620. A similar approach is made to set the core drill 560 for making the shaped bore to receive a guide hub 220 (FIG. 5*e*). In this way, the lengths of the tools required can be set based on only the baseline length being measured by the user.

In this example, a first offset 650 of 1 mm and a baseline length of 100 mm would result in the facing tool 540 being prepared to a length of 101 mm from datum 503 (or representative datum 503') for preparing a flat face on a skull during surgery. In other examples, the offset may be negative, that is to say the offset may be a protrusion on the datum surface 621 extending towards the tool aligning device 610. In such an example, if the first offset 650 is −2 mm (i.e. a 2 mm protrusion towards the tool aligning device 610) and the baseline length is 100 mm, the tool concerned would be set at 98 mm from datum 503 for surgery.

Figure 25A:
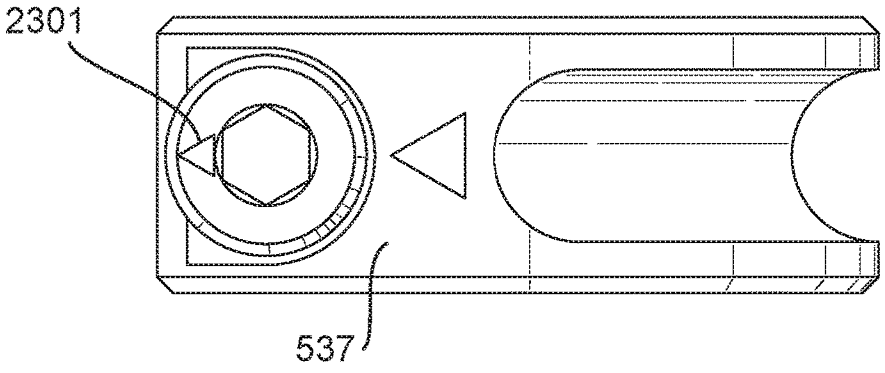
FIGS. 25*a* to 25*c* show a datum marker having an indicator for indicating if the datum marker is locked to a tool.
Figure 25B:
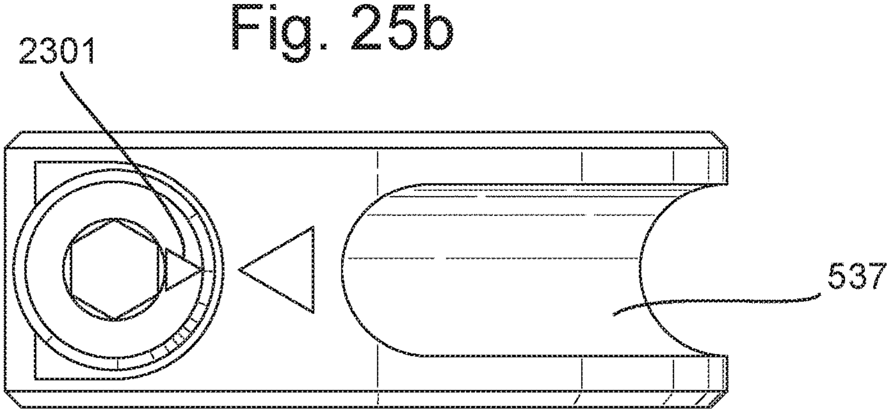
Figure 25C:
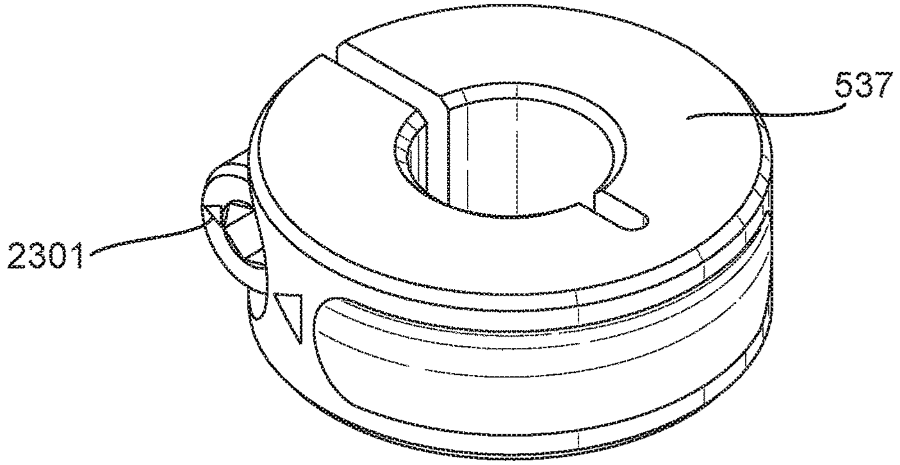

In the above examples, each tool 540, 550, 560 is fitted with a tool datum marker 537, 538, 539 that can be used in conjunction with a stereoguide to progress the tool into the skull to a carefully measured depth. The datum marker 537, 538, 539 may comprise an indicator 2301 that indicates whether the datum marker 537, 538, 539 is locked to the tool, or in an unlocked state where it can be moved up or down the tool. An example of such an indicator 2301 is shown in FIGS. 25*a* to 25*c*. In FIGS. 25*a* to 25*c*, the datum marker 537, 538, 539 uses a screw, which is tightened to fit the datum marker 537, 538, 539 to the tool. FIG. 25*a* shows the indicator 2301 in the unlocked position and FIG. 25*b* shows the indicator 2301 in the locked position. The indicator 2301 allows the user to rapidly determine if the datum marker 537, 538, 539 is locked, to reduce the chance of accidentally moving the datum marker 537, 538, 539 if the tool is removed from the jig with the datum marker 537, 538, 539 not locked to the tool. The depth stop 1806 of the insertion tool 570 may be provided with a similar indicator 2301 to indicate when it is locked onto the insertion tool.

The jig 600 may also be used in a similar fashion, to assist in inserting a guide hub 220 as illustrated in FIGS. 5*e* and 5*f*. The hub insertion tool 570 may be set with an appropriate length in the jig 600, making use of a tool datum marker to avoid over insertion of a hub 220 into the skull.

The use of the jig 600 to prepare surgical tools or devices for delivery through a guide hub 220 into the brain is now described.

Devices that may be delivered through a guide hub 220 include guide tubes, electrodes and cannulas, however it will be understood that other types of device may be delivered through the hub 220.

Referring still to FIG. 9, the reference guide 620 comprises a through-channel 653 for allowing passage of a device or tool therethrough, so that the device can extend downwards to the surface 631 of the cutting or measuring guide 630. In this example, the reference guide 620 includes a guide hub 220 fitted into a suitably shaped offset in the datum surface 621. This allows a hollow hub introducer tool 570 to be inserted into the hub 220 in the jig 600. A tool such as a track making probe 596 can be passed through the hub introducer tool 570, the hub 220 in the jig 600 and the reference guide 620.

In this way, the length of a device or tool required to extend from the hub 220 can be set in the jig 600. In this example, if the track making probe 596 is to prepare a track within the brain, the length of the probe 596 from the hub 220 to the desired position in the brain can be set as follows. The insertion tool 570, hub 220 and probe 596 combination are arranged as shown in FIG. 9. A first grub screw 595, operated by finger gripping, is located on the tool 570 for clamping the (thicker) proximal end 596*a* of the probe 596 passing through. A second grub screw 595*a* (with an allen key socket) is provided for clamping a datum marker in the form of a collar 536*a*, to the proximal end 596*a* of probe 596. Collar 536*a* provides a depth stop against the top surface of the insertion tool 570. The use of different screw types, a finger operated grub screw 595 and an allen key operated grub screw 595*a*, aids an operator to use the correct screw when working with the tools.

As shown in FIG. 9, the track making probe 596 extends to cutting or measuring guide 630. Datum marker 536*a* is then fixed to the proximal end 596*a* of the track making probe 596 by tightening grub screw 595*a*. The probe can then be retracted into the body of insertion tool 570 as suggested by arrow A, and held in position by tightening the first grub screw 595 by hand. The insertion tool, hub and probe assembly (570, 220,596) can then be removed from the jig and transferred to a patient. The guide hub 220 can be inserted into position (FIG. 5*f*) and the track making probe 596 then inserted through hub 220 to the depth set on the jig—where datum marker 536*a* rests against the top surface of the insertion tool 570. Thus, the fitting of the guide hub 220 to a patient's skull and making a track along a trajectory can be combined into one operation, with one use of the insertion tool 570.

In this example of the jig, the reference guide 620 comprises a first indicator 623 in the form of a first pointer which indicates a point on a scale 624. The scale 624 provides measurement along one side of the jig 600. The scale 624 provides a distance from the target datum 641 of the lower cross member 640. Using this scale 624, a surgeon can set the position of the reference guide 620, if the baseline length is not provided by a datum measurement tool 535. If, as in the present example, a datum measurement tool 535 is used, the set baseline length can be confirmed using the scale 624. The cutting or depth measuring guide 630 also has an indicator 633 in the form of a pointer which runs along scale 624. Using this second indicator 633, the position of the measuring guide 630 can be set based on a measurement provided by imaging studies of the patient.

A surgeon may set all of the tools and devices before starting surgery on the patient by making use of the jig 600. This may be manually or by computer control of a motorised jig, making use of scan data and the surgical planning software. Alternatively, the surgeon may set the reference guide 620 and measuring guide 630 and then set tools or devices on the jig 600 as required throughout a surgical procedure. The hub insertion tool 570 or another tool of the same type may be used to deliver a track making probe 596 into the brain of the patient, and then be set again on the jig 600 with the next device to be inserted into the brain. In FIG. 9, a further insertion tool, a guide tube insertion tool 570*a* is used to deliver a second probe 597. The second probe in this instance is used to deliver guide tube 598 and to create a track in the brain to target 501. In the example shown in FIG. 9, the second probe 597 is set to penetrate into the brain to the full depth permitted by the jig. The distal end of second probe 597 set onto the upper surface (target datum 641) of the lower cross member 640.

The jig 600 can also be used to set guide tubes and cannulas. The reference guide 620 comprises a profiled hole 561 which can match the depth within the throughbore of a guide hub 220. A guide tube 598 is located in the profiled hole 561 and extends downwards. The guide tube can then be cut to the desired length for insertion into the brain. The position to cut the guide tube 598 can be measured using scale 624 to set the position of guide 630 and the cut can be made using a knife passing through cutting slot 634.

The jig 600 is also shown for setting a cannula 599. A cap 300 carrying the cannula 599 is fitted into the reference guide 620 in a profiled hole corresponding to the internal through bore of a guide hub. The cannula 599 can then be cut to length by a knife inserted through cutting slot 635. As shown in FIG. 9 the cannula can be attached to a screwdriver 591 when being set in the jig 600. The screwdriver and cannula combination can then be removed from the jig for insertion into a patient.

Another jig 700 is now described with reference to FIGS. 10*a* and 10*b*. As can be seen in perspective view FIG. 10*b* the jig 700 includes side plates 797 that support the rectangular frame at an angle of 45 degrees to the horizontal. This allows easy fitting of tools and devices to the jig and lets gravity assist in locating them correctly in position. In this example the jig includes a back plate 798 against which tools or devices may rest. Like components to the jig 600 of FIG. 9 are designated by similar reference numerals with the addition of 100, e.g. the reference guide 720 is generally similar in function to the reference guide 620 in FIG. 9.

The jig 700 comprises a lower cross member 740 but a datum 741 corresponding to the location of a target (501 in FIG. 5*a*) is provided as the bottom end of scale 724; as slot 743 in cutting device 742; and also as platform 755. Thus, the distance from stereoguide datum 503 to a target 501 (FIG. 5*a*) is represented on the jig 700 by the scale 724, i.e. by the vertical distance from representative datum 503' to datum 741.

The jig 700 further comprises a second cutting device 744 with a corresponding second cutting slot 745.

A convenient use of a hollow insertion tool 770 is now described with reference to FIGS. 10*a* and 10*b*. The insertion tool 770 is similar to the tool 570 shown in previous figures. As with the corresponding arrangement shown in FIG. 9 the tool 770 features a double grub screw arrangement. A first grub screw 795 is located on the tool 770 for clamping a device passing through t. A second grub screw 796 is provided for clamping a datum marker 799 to the device thereby providing a stop against the top surface of the screwdriver 790.

Figure 10A:
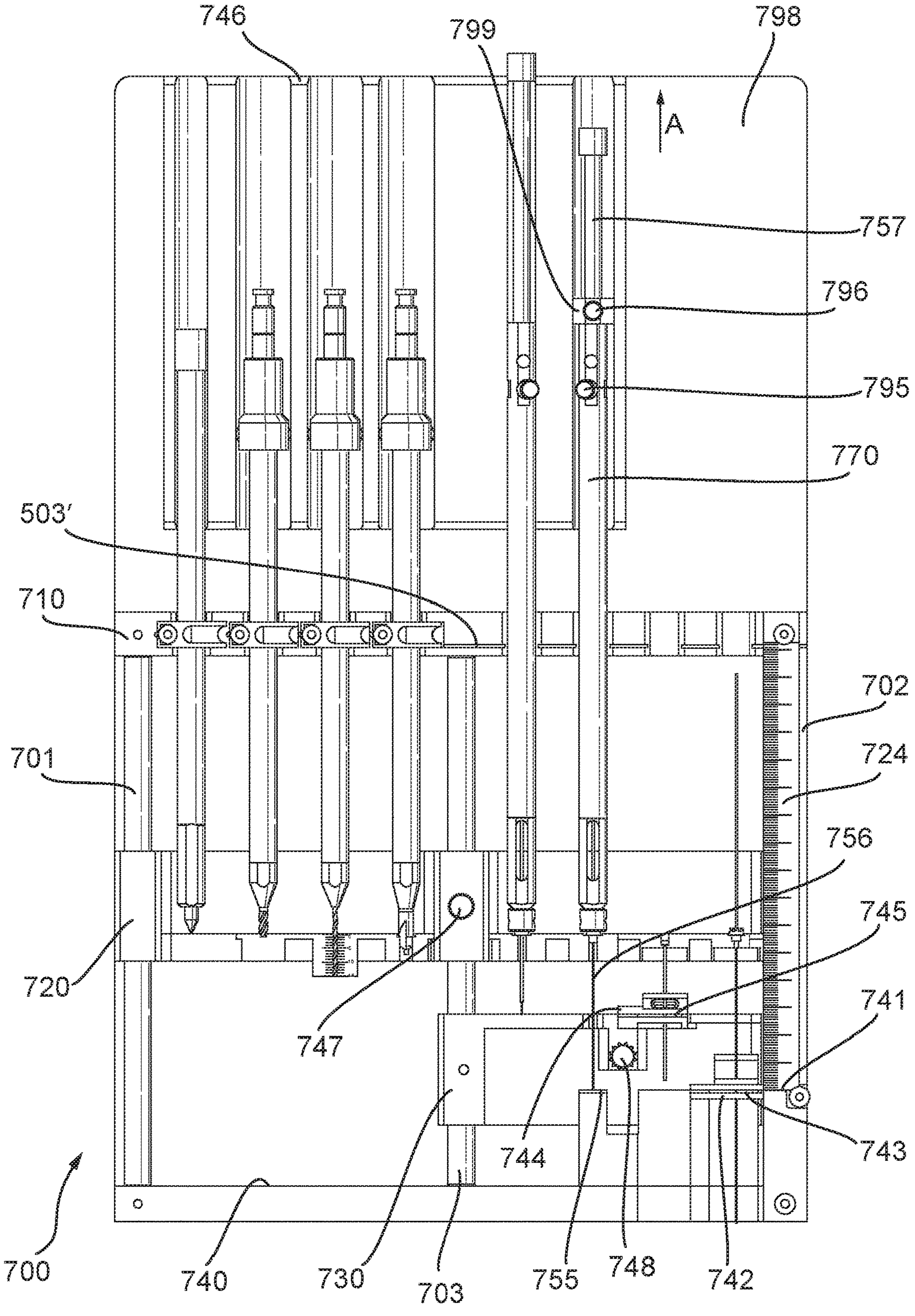
FIGS. 10*a* and 10*b* show an alternative jig in accordance with the present invention.
Figure 10B:
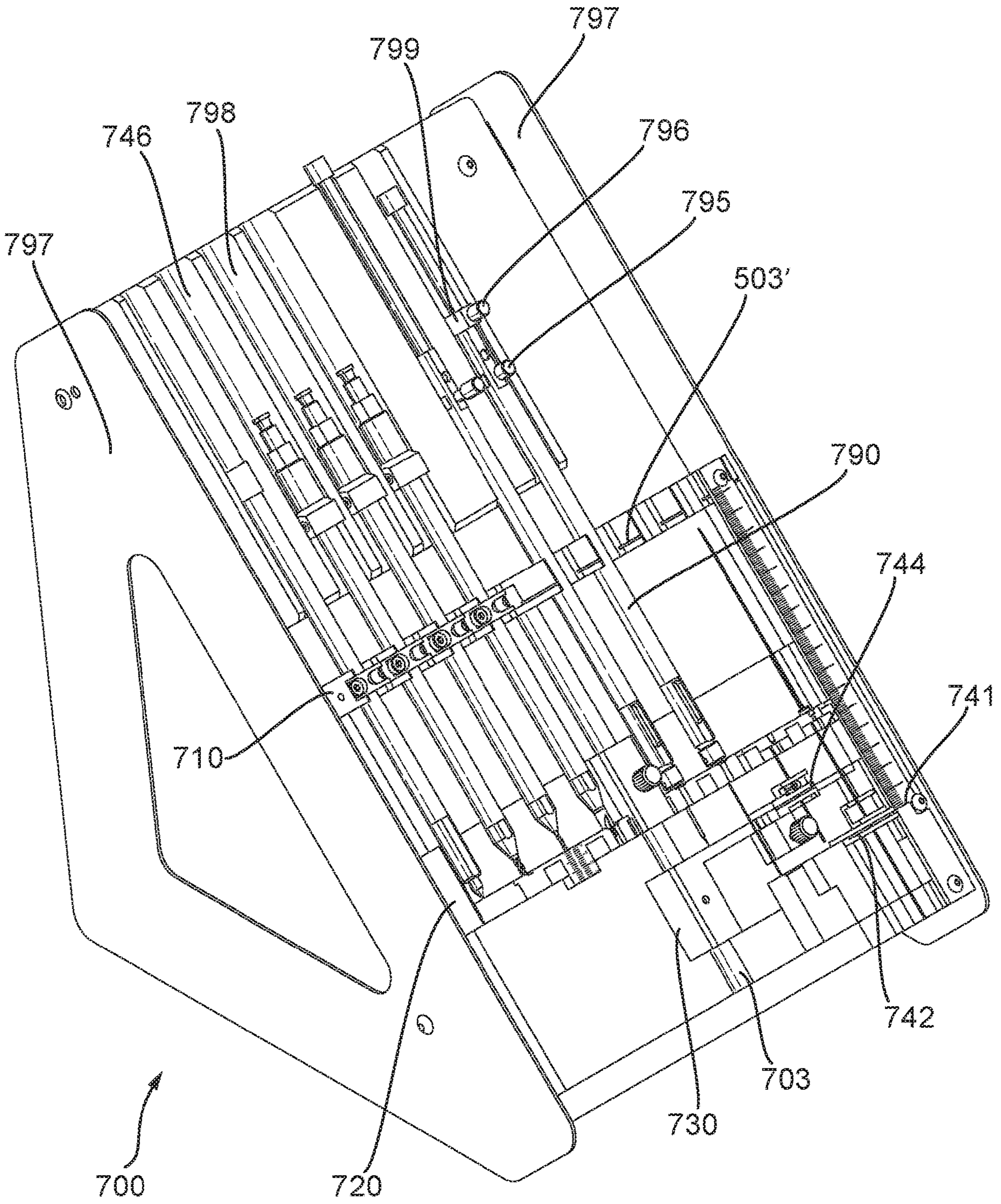

As shown in FIG. 10*a*, a probe 756 extends to platform 755. Datum marker 799 is then fixed to the distal end of the probe 757 by tightening grub screw 796. The probe can then be retracted into the body of tool 770 as suggested by arrow A, and held in position by tightening the first grub screw 795. The tool and probe assembly can then be fitted to a guide hub in a patient's skull and grub screw 595 released to allow driving the probe 756 into the patient's brain to the depth previously set on the jig (platform 755).

In the jig 700, the reference guide 720 and cutting or depth measuring guide 730 are moveable and lockable.

As shown in FIG. 10*a* the jig 700 comprises two parallel outer guide rails 701 and 702 and a central guide rail 703 which is parallel to the two outer guide rails 701, 702. The central guide rail 703 connects the lower cross member 740 to the reference guide 720. The lower cross member 740 and back plate 798 provide stability and rigidity to the jig 700. In this example the back plate also includes a number of grooves 746 for accepting the bodies of tools being set.

The outer guide rails 701, 702 provide a means by which the reference guide 720 and the cutting or measuring guide 730 can be moved whilst remaining parallel to each other and to the tool aligning device 710. The reference guide 720 has a first locking screw 747 which can be turned to clamp the reference guide 720 to the central guide rail 703. Thus the reference guide 720 can be fixed in a selected position. The measuring guide 730 comprises a similar second locking screw 748 which screws down onto the backplate 798 for locking engagement.

Figure 11:
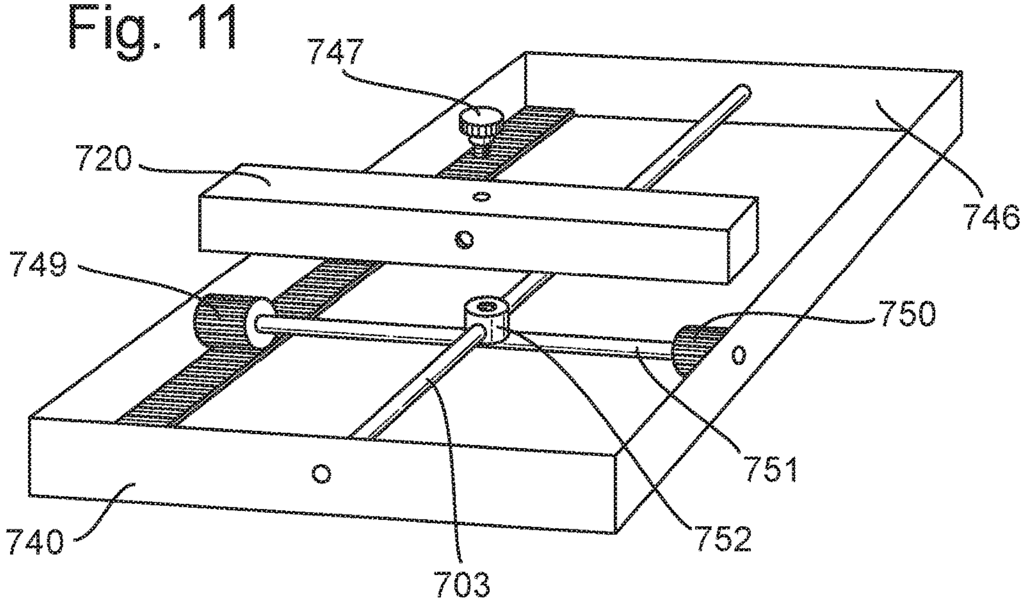
FIGS. 11, 12, and 13 show schematic views of components of a jig.
Figure 12:
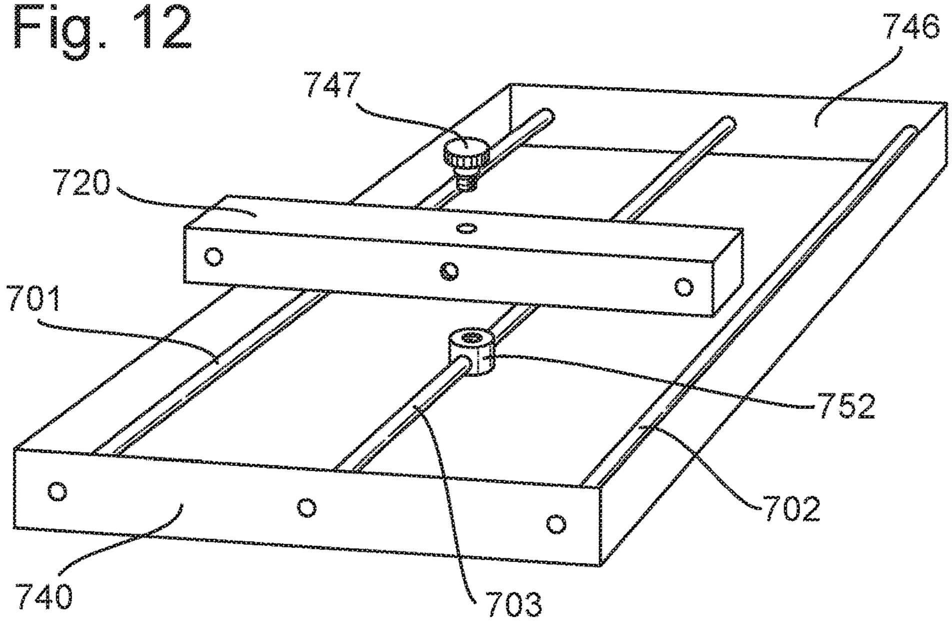

FIGS. 11 and 12 show schematically mechanisms that can be employed to move and lock into place a reference guide or a measuring guide. Similar mechanisms may be employed with the jig of FIG. 9 or that of FIG. 10.

In partially exploded view FIG. 11, a first example of a tracking system is shown. Reference guide 720 and screw 747 are shown detached from their locations for ease of viewing. To allow the reference guide 720 to move up and down whilst remaining parallel to a tool aligning device, the jig 700 is provided with a rack and pinion arrangement. First and second rack and pinion sets 749, 750 are provided at the outer guide rails 701, 702. As shown in FIG. 11, the reference guide 720 is attached to a cross member 751 which connects the pinions of the rack of the rack and pinion sets 749, 750.

A cutting and measuring guide can also be arranged to move in the same fashion.

As illustrated, the reference guide 720 is also attached to the central guide rail 703 such that it can slide up and down the central guide rail 703 when unlocked, and be locked to the central guide rail 703 by use of a first locking screw 747.

Alternatively, as shown in partially exploded view FIG. 12, the reference guide 720 may be moveable in sliding engagement on the first and second outer guide rails 701, 702. The outer guide rails 701, 702 pass through holes in the reference guide 720 to allow it to slide up and down in the jig until held locked in place by screw 747.

Figure 13:
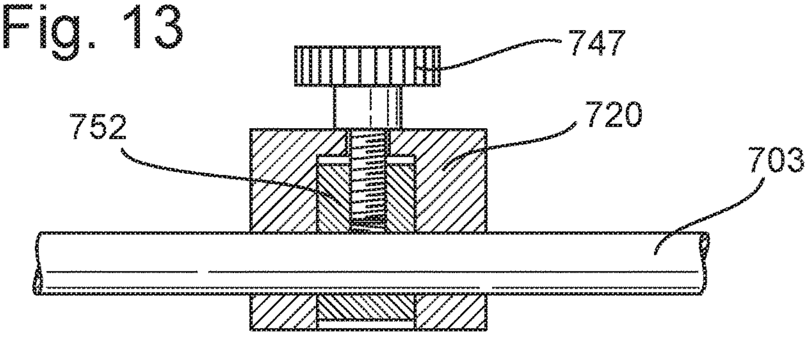

FIG. 13 an exemplary locking mechanism of the first locking screw 747. The same mechanism may be used for a second locking screw 748. FIG. 13 shows a cross-sectional view through the first locking screw 747 and through the width of the reference guide 720 as it is in position in the jig 700. The first locking screw 747 is received in a threaded hole in the reference guide 720 and in a threaded hole in a first locking screw block 752. Engagement with the first locking screw block 752 lifts and engages the first locking screw block 752 with the central guide rail 703. If the first locking screw 747 is screwed to a maximal extent, the first locking screw 747 itself engages the central guide rail 703 thereby additionally securing the moveable reference guide 720 to the central guide rail 703. Alternatively, a simpler arrangement may be provided whereby the first locking screw 747 engages the central guide rail 703 directly to lock the moveable reference guide 720 to central guide rail 703. For example, a locking screw with a nylon thread or a nylon end has been found to give a good gripping action.

In some arrangements it may be desirable to provide particularly fine adjustments to the positioning of a reference guide or a cutting and measuring guide. If so the central guide rail 703 may be screw threaded where it fits to lower cross member 740 (not shown). Rotation of the guide rail 703 can then be used to give small movement of the reference guide or cutting and measuring guide in the jig frame.

Figure 14A:
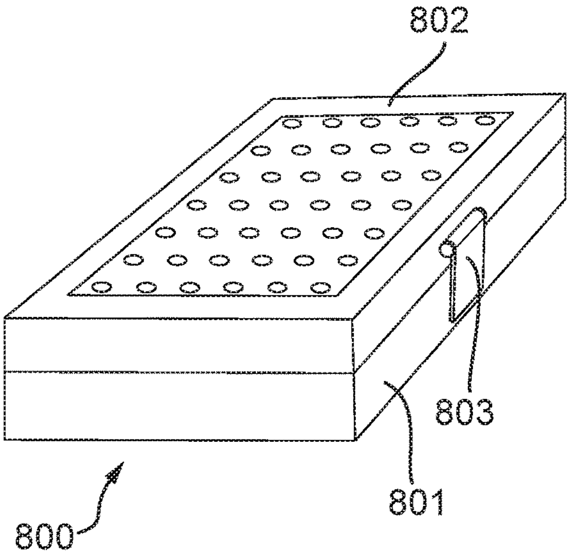
FIGS. 14*a* to 14*c* show a jig combined with sterilisation tray.
Figure 14B:
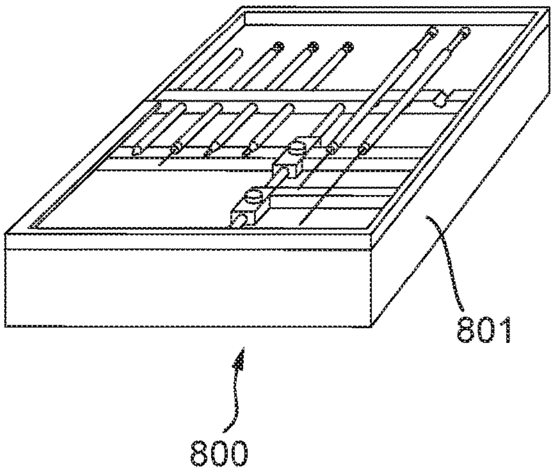
Figure 14C:
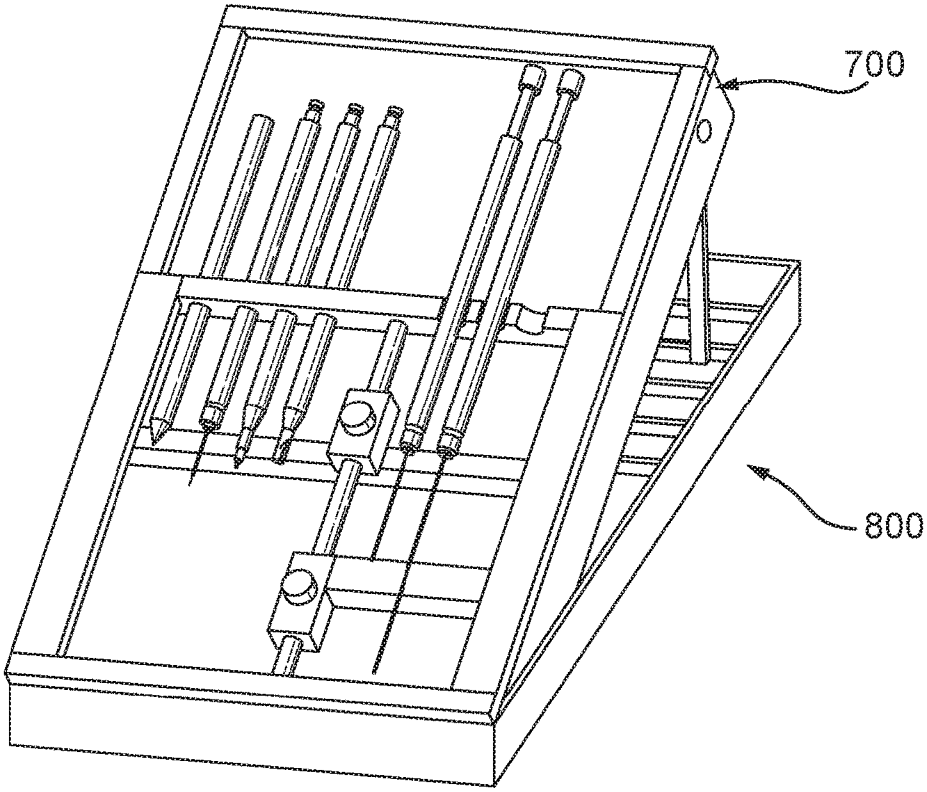
Figure 15A:
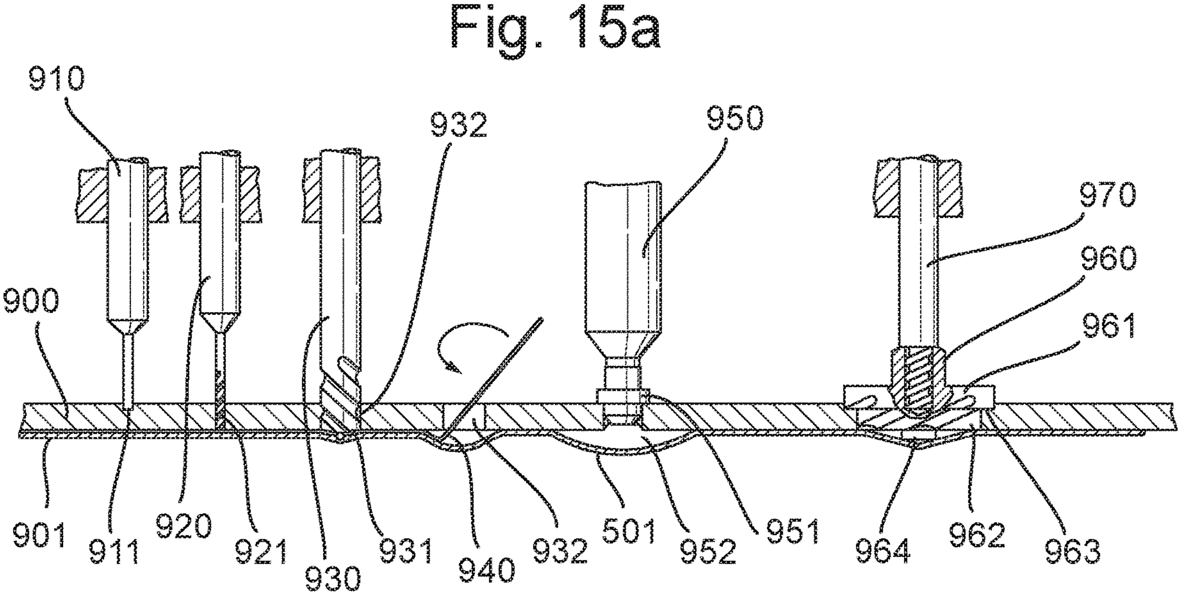
FIG. 15*a* shows a method of preparing the surface of the skull for delivery of a deep brain stimulation generator.
Figure 15B:
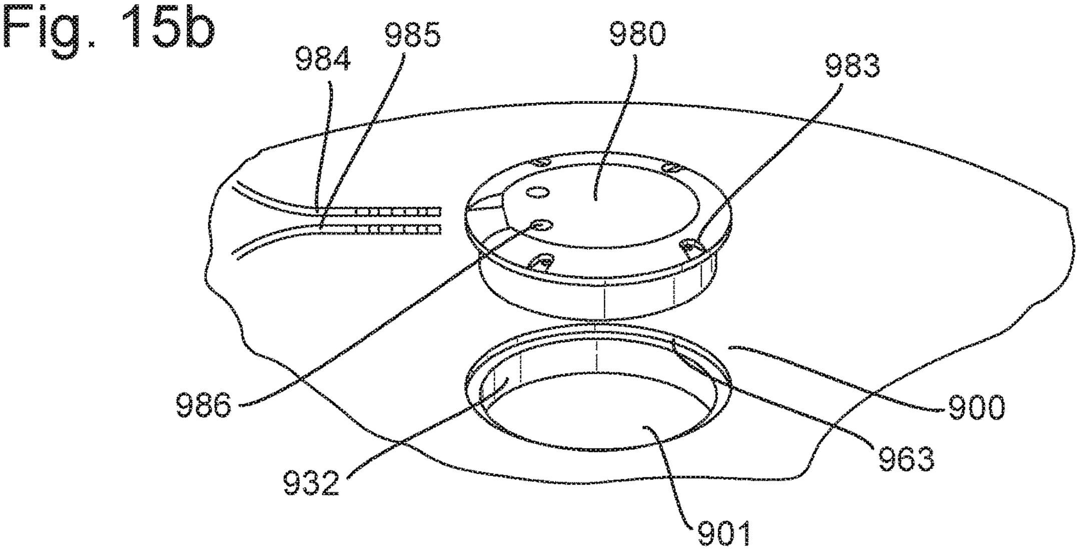
FIG. 15*b* shows a DBS generator being delivered into a hole in the skull.
Figure 15C:
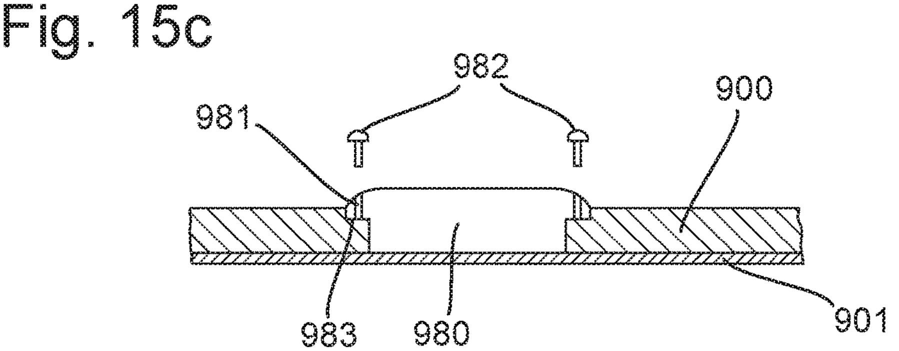
FIG. 15*c* shows the DBS generator of FIG. 6*b* being secured into the skull by screws.

FIGS. 14*a* to 14*c* show a sterilisation tray and case for the jig 700. It is preferable that the jig 700 is provided at an angle during use, thereby allowing tools to be moved under gravity into the desired locations. When not in use the jig can be stored, preferably in a sterile, ready to use condition. FIG. 14*a* shows a sterilisation tray 800 comprising a lower tray 801 and an upper tray 802. The upper and lower trays 801, 802 together form a protective housing for the jig 700 and associated instruments or devices held therein. The upper and lower tray 801, 802 are held together by a clasp 803. The tray 800 provides protection for the jig 700 and tools therein during transport and storage. When the jig 700 is to be used, the upper tray 802 can be removed as shown in FIG. 14*b*. The lower tray 801 forms the base support for the jig 700 to which it is attached by a hinge at its distal end. In use the proximal end of the jig is raised to create a 45° angle with respect to the base as the distal end rotates about the hinge. A support bar or bars that were folded behind the jig 700 are now brought into engagement with features on the inside base of the tray 801 to provide a stable fixation of the jig at 45° during the surgical procedure as shown in FIG. 4*c*. Conveniently after use the instruments are repositioned in the jig 700 and the support bars folded behind the jig so that it can be laid flat for re-sterilisation, maintaining the instruments in the order in which they will be used in a subsequent procedure. FIGS. 15*a*, 15*b* and 15*c*, show tool that have been set using a jig of the invention when employed in fitting a skull mounted Deep Brain Stimulation (DBS) battery power supply (a 'generator').

FIG. 15*a* shows a sequence of events in preparing a hole in a patient's skull, from left to right. The skull 900 and dura layer 901 beneath the skull are shown in cross section. To install a DBS generator 980 (shown in FIG. 15*b*) in the skull 900, a stereotactic frame or robot is arranged around the head of a patient. A baseline length setting in a jig 700 is obtained as previously described. This baseline length sets the jig 700 such that the tools which are required can be set in generally the same manner as described previously.

Starting from the left hand illustration of FIG. 15*a* a facing tool 910 is used to form a flat surface 911 on the skull 900. A pilot drill 920 then drills a pilot hole 921, which is then opened out by a core drill 930 comprising a nib 931 for maintaining directing the core drill 930 within the pilot hole 921 as the core drill 930 advances through the skull 900. A blunt hook 940 is manually inserted to free the dura 901 from the skull 900 in the vicinity of the enlarged hole 932. A gel dispensing container 950 is then brought to the enlarged hole 932 and butts against the enlarged hole 932 with the aid of a stop 951. Haemostatic gel 952 is then delivered through the enlarged hole 932, providing a protective barrier separating the dura 901 from the skull 900 and preventing excessive bleeding.

A milling tool 960 then mills around the enlarged hole 932 previously created by the core drill 930. The milling tool 960 in this example comprises a first mill body 961 and a second mill body 962. The first mill body 961 has a cutting surface that opens the enlarged hole 932 to a first diameter and the second mill body 962 has a cutting surface opens the enlarged hole to a second diameter, smaller than the first diameter. In this way, a ledge 963 is created within the hole. The milling tool 960 further comprises a blunt nib 964 which is sized and dimensioned to locate within the enlarged hole 932 during milling, thereby providing stabilisation and ensuring the milling tool 960 remains on its desired trajectory. The milling tool 960 is attached to the threaded shaft 970 enabling the attachment of the larger diameter milling tool below the stereoguide which is of a smaller diameter. As an alternative two milling tools, with different diameters, may be employed to form the hole including a ledge.

After the above steps the hole prepared in the skull is then ready to receive the DBS generator 980 as will now be explained with reference to FIGS. 15*b* and 15*c*.

In FIG. 15*b*, the hole 932 created by the milling tool 960 can be seen. The dura 901 below the skull is visible through the hole 932. The circular DBS generator 980 is now inserted into the hole 932 by either pressing the DBS generator 980 into the hole 932 by hand, by robot or with guidance of a stereotactic frame and a suitable installation tool (not shown). In the method shown, the surgeon simply inserts the DBS generator 980 by hand until the DBS generator 980 is seated within the hole 932. As can be seen in FIG. 15*c* the DBS generator 980 comprises a circumferential stop 981 configured to engage with the ledge 963, to avid over-insertion of the DBS generator 980. The surgeon can then attach the DBS generator 980 to the skull 900 using a set of screws 982 which are located within corresponding holes 983.

Electrical cables 984, 985 can then be attached to the DBS generator 980 by inserting the cables 984, 985 through correspondingly dimensioned holes in the DBS generator 980. The cables 984, 985 are secured to the DBS generator 980 by a second sets of grub screws (not shown) which are located within corresponding second grub screw holes 986 or by operating captured cam-locks that engage with the lateral aspect of the inserted DBS electrode leads 984, 985 that are implanted through the skull of the patient to brain targets.

The DBS generator 980 may be around 2 cm-6 cm in diameter. Alternatively, the DBS generator 980 may be around 3-4 cm in diameter.

Figure 16A:
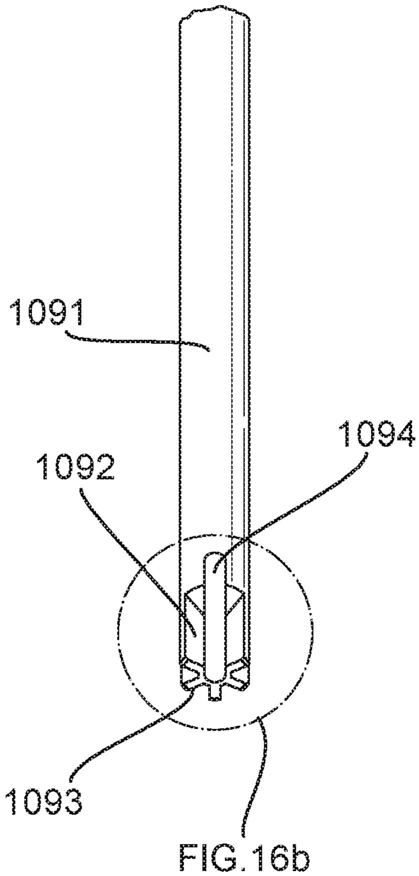
FIG. 16*a* shows, in perspective view from below, the distal end of a screwdriver.
Figure 16B:
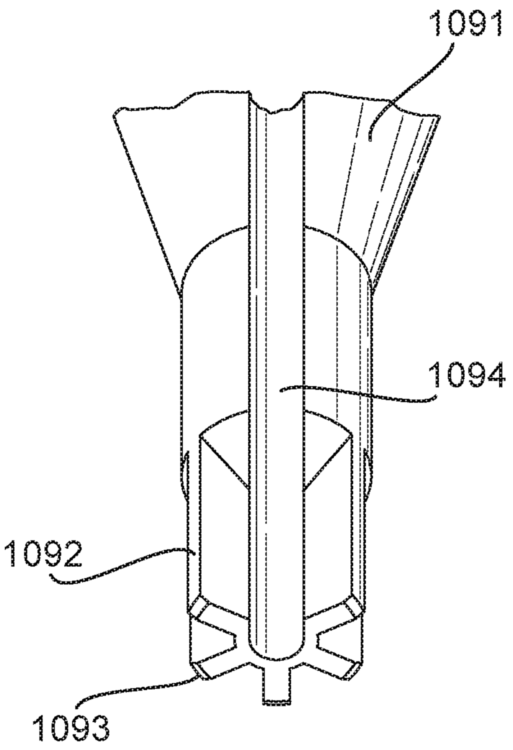
FIG. 16*b* shows a magnification of part of FIG. 16*a;*

FIG. 16*a* shows, in perspective view from below, the distal end of a screwdriver 1091 of similar function to that of FIG. 8. FIG. 16*b* shows a magnification of the distal end. As can be seen from these figures the hexalobular formation 1092 has one lobe missing to allow the side slot 1094 to extend to the extreme distal end 1093 of the tool. Thus, the side slot allows fitting of the screwdriver 1091 over a cap when fitting and/or removing a device such as a cannula as discussed above and with reference to FIGS. 7 and 8.

The invention claimed is:

1. A jig for setting the depth of insertion of a surgical tool into a patient during surgery, the jig comprising:

a tool aligning device;

a representative datum representing a stereoguide datum; and a reference guide moveable relative to the representative datum to set a baseline length from the representative datum to a datum surface on the reference guide;

wherein the reference guide comprises at least one offset from the datum surface configured to receive a surgical tool extending from the tool aligning device; and wherein the depth of insertion of the surgical tool when used in surgery on a patient is set on the jig by the distance from the representative datum to the offset; and wherein the tool aligning device comprises a bar including slots or grooves to receive generally elongate tools and direct their distal ends towards the reference guide.

2. The jig of claim 1, wherein the tool aligning device comprises the representative datum.

3. The jig of claim 1, further comprising a target datum, representing a target position with respect to a stereoguide datum as used in a chosen stereotactic system or arrangement.

4. The jig of claim 1, wherein the reference guide is moveable, and the representative datum fixed.

5. The jig of claim 1, further comprising a stand to hold the jig up from an angle to the horizontal.

6. The jig of claim 1 wherein the moveable reference guide is in a form of a bar parallel to the bar of the tool aligning device and is moveable relative to the tool aligning device whilst retaining the parallel relationship.

7. The jig of claim 1 wherein:

the reference datum is provided on the bar of the tool aligning device;

the reference guide comprises a bar parallel to the bar of the tool aligning device and is moveable relative to the tool aligning device whilst retaining the parallel relationship;

the bars of the tool aligning device and the reference guide are connected by at least two rails, the at least two rails disposed one at each end of the bar of the tool aligning device and connecting to corresponding ends of the bar of the moveable reference guide.

8. The jig of claim 7 wherein the bar of the reference guide is in sliding engagement with the at least two rails.

9. The jig of claim 7, wherein there are at least three rails connecting the tool aligning device and the reference guide, with the third rail disposed at a midpoint of the bar of the tool aligning device and extending to a corresponding midpoint of the bar of the reference guide.

10. The jig of claim 7 wherein either:

the at least two rails are threaded and operate as lead-screws passing through corresponding threads on the bar of the reference guide; or the at least two rails comprise rack gears and the bar of the reference guide comprises corresponding pinions.

11. The jig according to claim 1, wherein the reference guide comprises at least one guide channel extending therethrough, for passage of a surgical tool, the guide channel extending from the datum surface and continuing in a direction set by the tool aligning device.

12. The jig of claim 1, wherein the tool aligning device is configured to receive one or more of:

a facing tool for creating a flat worksurface on a bone;

a pilot drill for creating a pilot hole in a bone; and a core drill for creating a profiled hole in a bone.

13. The jig of claim 1, wherein the reference guide further comprises a hole for receiving a surgical guide hub for implanting in an aperture formed in a skull and made along a trajectory to a brain target, wherein the guide hub includes:

a through-bore for delivering a device therethrough and along the trajectory;

at least one first formation on an external surface for securing the hub within the aperture in a skull; and at least one second formation on the surface of the through-bore for securing a guide device, an implantable device, or a cap to the hub.

14. The jig of claim 13, wherein the reference guide includes a guide channel therethrough for passage of a surgical tool through the reference guide and a surgical guide hub located in the hole.

15. The jig of claim 1, further comprising a moveable cutting or depth measuring guide disposed further from the tool aligning device than the reference guide and for adjusting to a selected length or cutting to a selected length a surgical tool or tool part extending from the datum surface through the moveable reference guide.

16. The jig of claim 15 wherein the moveable cutting or depth measuring guide comprises a bar parallel to both the aligning device and the reference guide and having a guide surface for engaging with the distal end of a surgical tool or tool part.

17. A system comprising a jig according to claim 1, and further comprising:

at least one surgical tool selected from the group consisting of:

a facing tool for creating a flat worksurface on a bone;

a pilot drill for creating a pilot hole in a bone;

a core drill for creating a profiled hole in a bone;

a milling tool to create a larger diameter profiled hole in the bone;

a surgical guide hub for insertion into the profiled hole, the surgical guide hub for implanting in an aperture formed in a skull and made along a trajectory to a brain target, and wherein the surgical guide hub comprises:

a through-bore for delivering a device therethrough and along the trajectory;

at least one first formation on an external surface for securing the surgical guide hub within the aperture in a skull; and at least one second formation on the surface of the through-bore for securing a guide device, an implantable device, or a cap to the surgical guide hub.

18. The system of claim 17, wherein the facing tool comprises a distal cylindrical cutter and a proximal cylindrical cutter, wherein the distal cylindrical cutter has a smaller diameter than the proximal cylindrical cutter.

19. A method of preparing an operative length of a surgical tool, comprising the steps of:

i) providing a system according to claim 17;

ii) setting a baseline length from the representative datum to a datum surface on the reference guide by moving the reference guide relative to the representative datum; and iii) moving a surgical tool in the tool alignment device into a pre-determined offset in the reference guide to obtain an operative length of the surgical tool.

20. The method of claim 19, wherein the step of setting the baseline length comprises the steps of:

iv) holding a datum measurement tool within the tool alignment device;

v) moving the reference guide relative to the tool alignment device to contact the distal end of the datum measurement tool; and vi) clamping the reference guide stationary at the length from the tool alignment device determined by the datum measurement tool.

21. A system for implantation of a cylindrical DBS generator in the skull, the system comprising:

a) a jig according to claim 1;

b) a facing tool for creating a flat worksurface on a bone;

c) a pilot drill for creating a pilot hole in a bone;

d) a core drill with for creating a hole larger than the pilot hole in a bone; and e) at least one milling tool for creating a profiled hole to accommodate a said cylindrical DBS generator within the skull.

22. The system of claim 21 wherein the at least one milling tool comprises:

a distal cutting surface for cutting a DBS generator mounting hole of a larger diameter than the core drill hole through the skull; and a proximal cutting surface for creating a ledge in the skull around the DBS generator mounting hole to accommodate a corresponding lip of the cylindrical DBS generator.

23. A jig for setting the depth of insertion of a surgical tool into a patient during surgery, the jig comprising:

a tool aligning device;

a representative datum representing a stereoguide datum;

a reference guide moveable relative to the representative datum to set a baseline length from the representative datum to a datum surface on the reference guide; and a stand to hold the jig up from an angle to the horizontal, wherein the reference guide comprises at least one offset from the datum surface configured to receive a surgical tool extending from the tool aligning device; and wherein the depth of insertion of the surgical tool when used in surgery on a patient is set on the jig by the distance from the representative datum to the offset.

24. A system comprising a jig according to claim 23, and further comprising:

at least one surgical tool selected from the group consisting of:

a facing tool for creating a flat worksurface on a bone;

a pilot drill for creating a pilot hole in a bone;

a core drill for creating a profiled hole in a bone;

a milling tool to create a larger diameter profiled hole in the bone;

a surgical guide hub for insertion into the profiled hole, the surgical guide hub for implanting in an aperture formed in a skull and made along a trajectory to a brain target, and wherein the surgical guide hub comprises:

a through-bore for delivering a device therethrough and along the trajectory;

at least one first formation on an external surface for securing the surgical guide hub within the aperture in a skull; and at least one second formation on the surface of the through-bore for securing a guide device, an implantable device, or a cap to the surgical guide hub.

25. A method of preparing an operative length of a surgical tool, comprising the steps of:

i) providing a system according to claim 24;

ii) setting a baseline length from the representative datum to a datum surface on the reference guide by moving the reference guide relative to the representative datum; and iii) moving a surgical tool in the tool alignment device into a pre-determined offset in the reference guide to obtain an operative length of the surgical tool.

* * * * *